(12) United States Patent
Lepek et al.

(10) Patent No.: US 11,723,349 B2
(45) Date of Patent: Aug. 15, 2023

(54) METHOD AND APPARATUS FOR SEX SORTING OF MOSQUITOES

(71) Applicant: Senecio Ltd., Kfar-Saba (IL)

(72) Inventors: Hanan Lepek, Kfar-Saba (IL); Tamir Nave, Kiryat-Ono (IL); Yoram Fleischmann, Kibbutz Lehavot Haviva (IL); Rom Eisenberg, Kfar-Saba (IL); Itamar Tirosh, RaAnana (IL)

(73) Assignee: Senecio Ltd., Kfar-Saba (IL)

( * ) Notice: Subject to any disclaimer, the term of this patent is extended or adjusted under 35 U.S.C. 154(b) by 687 days.

(21) Appl. No.: 16/628,730

(22) PCT Filed: Jul. 6, 2018

(86) PCT No.: PCT/IL2018/050738
§ 371 (c)(1),
(2) Date: Jan. 6, 2020

(87) PCT Pub. No.: WO2019/008591
PCT Pub. Date: Jan. 10, 2019

(65) Prior Publication Data
US 2020/0281164 A1   Sep. 10, 2020

Related U.S. Application Data

(60) Provisional application No. 62/668,842, filed on May 9, 2018, provisional application No. 62/647,934, filed (Continued)

(51) Int. Cl.
*A01K 67/033* (2006.01)
*A01K 1/08* (2006.01)
(Continued)

(52) U.S. Cl.
CPC .......... *A01K 67/033* (2013.01); *A01K 1/08* (2013.01); *A01K 29/00* (2013.01); *G06F 18/2431* (2023.01); *G06N 5/025* (2013.01)

(58) Field of Classification Search
CPC ........ A01K 29/00; A01K 1/08; A01K 67/033; G06N 5/025; G06F 18/2431
See application file for complete search history.

(56) References Cited

U.S. PATENT DOCUMENTS 7,496,228 B2   2/2009   Landwehr et al.
7,916,951 B2   3/2011   Landwehr et al.
(Continued)

FOREIGN PATENT DOCUMENTS

CN   103188939   7/2013
CN   203913006   11/2014
(Continued)

OTHER PUBLICATIONS

Notification of Office Action and Search Report dated Nov. 10, 2021 From the State Intellectual Property Office of the People's Republic of China Re. Application No. 2018800075.86.0 and Its Translation of Office Action Into English. (9 Pages).
(Continued)

*Primary Examiner* — Monica L Perry
*Assistant Examiner* — Aaron M Rodziwicz

(57) ABSTRACT

Method of providing insects for sorting into classes or for quality control of sorted insects comprises providing the insects in a container having a closable opening, opening the closable opening, releasing the insects through the closable opening onto a funneled air flow, the air flow carrying the insects to a collection location, the collection location being conveyable, and applying immobilizing agent to the insects on the collection location, thereby to provide stationary insects for said sorting or quality control.

22 Claims, 37 Drawing Sheets

Related U.S. Application Data on Mar. 26, 2018, provisional application No. 62/533,242, filed on Jul. 17, 2017, provisional application No. 62/529,057, filed on Jul. 6, 2017.

(51) Int. Cl.
*A01K 29/00* (2006.01)
*G06N 5/025* (2023.01)
*G06F 18/2431* (2023.01)

(56) References Cited

U.S. PATENT DOCUMENTS

| | | | |
|---|---|---|---|
| 8,755,571 B2 | 6/2014 | Tsai et al. | |
| 9,180,464 B2 | 11/2015 | Nimmo et al. | |
| 10,542,736 B2 * | 1/2020 | Yao | C05F 17/05 |
| 11,291,190 B1 * | 4/2022 | Peeters | A01K 67/033 |
| 2003/0188698 A1 * | 10/2003 | Donaldson | A01K 67/033 |
| | | | 119/678 |
| 2005/0025357 A1 | 2/2005 | Landwehr et al. | |
| 2005/0100532 A1 | 5/2005 | Hoffman et al. | |
| 2010/0058645 A1 * | 3/2010 | Reime | A01M 3/00 |
| | | | 43/111 |
| 2012/0189549 A1 * | 7/2012 | Claridge-Chang | A01K 29/005 |
| | | | 600/300 |
| 2014/0226860 A1 | 8/2014 | Hyde et al. | |
| 2015/0023566 A1 | 1/2015 | Fryshman | |
| 2016/0135754 A1 | 5/2016 | Marshall et al. | |
| 2018/0092339 A1 | 4/2018 | Massaro et al. | |
| 2018/0121764 A1 | 5/2018 | Zha et al. | |
| 2020/0154685 A1 | 5/2020 | Lepek et al. | |
| 2020/0154686 A1 | 5/2020 | Lepek et al. | |
| 2021/0022326 A1 | 1/2021 | Lepek et al. | |
| 2022/0053743 A1 * | 2/2022 | Lepek | B07B 1/22 |

FOREIGN PATENT DOCUMENTS

| | | |
|---|---|---|
| EP | 0427305 | 10/1990 |
| JP | 11-266741 | 10/1999 |
| WO | WO 2009/067089 | 5/2009 |
| WO | WO 2013/082700 | 6/2013 |
| WO | WO 2016/088129 | 6/2016 |
| WO | WO 2017/158216 | 9/2017 |
| WO | WO 2018/067376 | 4/2018 |
| WO | WO 2018/134828 | 7/2018 |
| WO | WO 2018/134828 A3 | 7/2018 |
| WO | WO 2018/134829 | 7/2018 |
| WO | WO 2019/008591 | 1/2019 |

OTHER PUBLICATIONS

Official Action dated Dec. 24, 2021 from US Patent and Trademark Office Re. U.S. Appl. No. 16/479,648. (30 pages).
Decision to Grant a Patent Right Invention dated Jul. 22, 2022 From the State Inellectual Property Office of the People's Republic of China Re. Application No. 201880050460.1. (4 Pages).
Search Report and Written Opinion dated Nov. 2, 2020 From the Intellectual Property Office of Singapore, IPOS Re. Application No. 11201906740Y. (11 Pages).
Official Action dated Feb. 16, 2021 From the US Patent and Trademark Office Re. U.S. Appl. No. 17/067,694. (16 Pages).
Final Official Action dated May 24, 2021 from the US Patent and Trademark Office Re. U.S. Appl. No. 17/067,694. (13 pages).
Restriction Official Action dated Aug. 27, 2021 from the US Patent and Trademark Office Re. U.S. Appl. No. 16/479,649. (7 pages).
Translation of Examination Report dated Jun. 2, 2022 From the Servico Publico Federal, Ministerio da Economia, Institute National da Propriedade Industrial do Brasil Re Application No. BR112020000262.3. ( 4 Pages).
Examination Report dated Jun. 2, 2022 From the Servico Publico Federal, Ministerio da Economia, Institute Nacional da Propriedade Industrial do Brasil Re Application No. BR112020000262.3. ( 4 Pages).
International Preliminary Report on Patentability dated Aug. 1, 2019 From the International Bureau of WIPO Re. Application No. PCT/IL2018/050080. (20 Pages).
International Preliminary Report on Patentability dated Dec. 21, 2018 From the International Preliminary Examining Authority Re. Application No. PCT/IL2018/050081. (19 Pages).
International Preliminary Report on Patentability dated Jan. 31, 2020 From the International Preliminary Examining Authority Re. Application No. PCT/IL2018/050738. (27 Pages).
International Search Report and the Written Opinion dated Jul. 8, 2019 From the International Searching Authority Re. Application No. PCT/IL2018/050738. (25 Pages).
International Search Report and the Written Opinion dated Sep. 21, 2018 From the International Searching Authority Re. Application No. PCT/IL2018/050080. (26 Pages).
International Search Report and the Written Opinion dated May 24, 2018 From the International Searching Authority Re. Application No. PCT/IL2018/050081. (15 Pages).
Invitation to Pay Additional Fees, Communication Relating to the Results of the Partial International Search and the Provisional Opinion dated Apr. 3, 2019 From the International Searching Authority Re. Application No. PCT/IL2018/050738. (16 Pages).
Invitation to Pay Additional Fees, Communication Relating to the Results of the Partial International Search and the Provisional Opinion dated Jun. 6, 2018 From the International Searching Authority Re. Application No. PCT/IL2018/050080. (18 Pages).
Written Opinion dated Oct. 23, 2019 From the International Preliminary Examining Authority Re. Application No. PCT/IL2018/050738. (15 Pages).

* cited by examiner

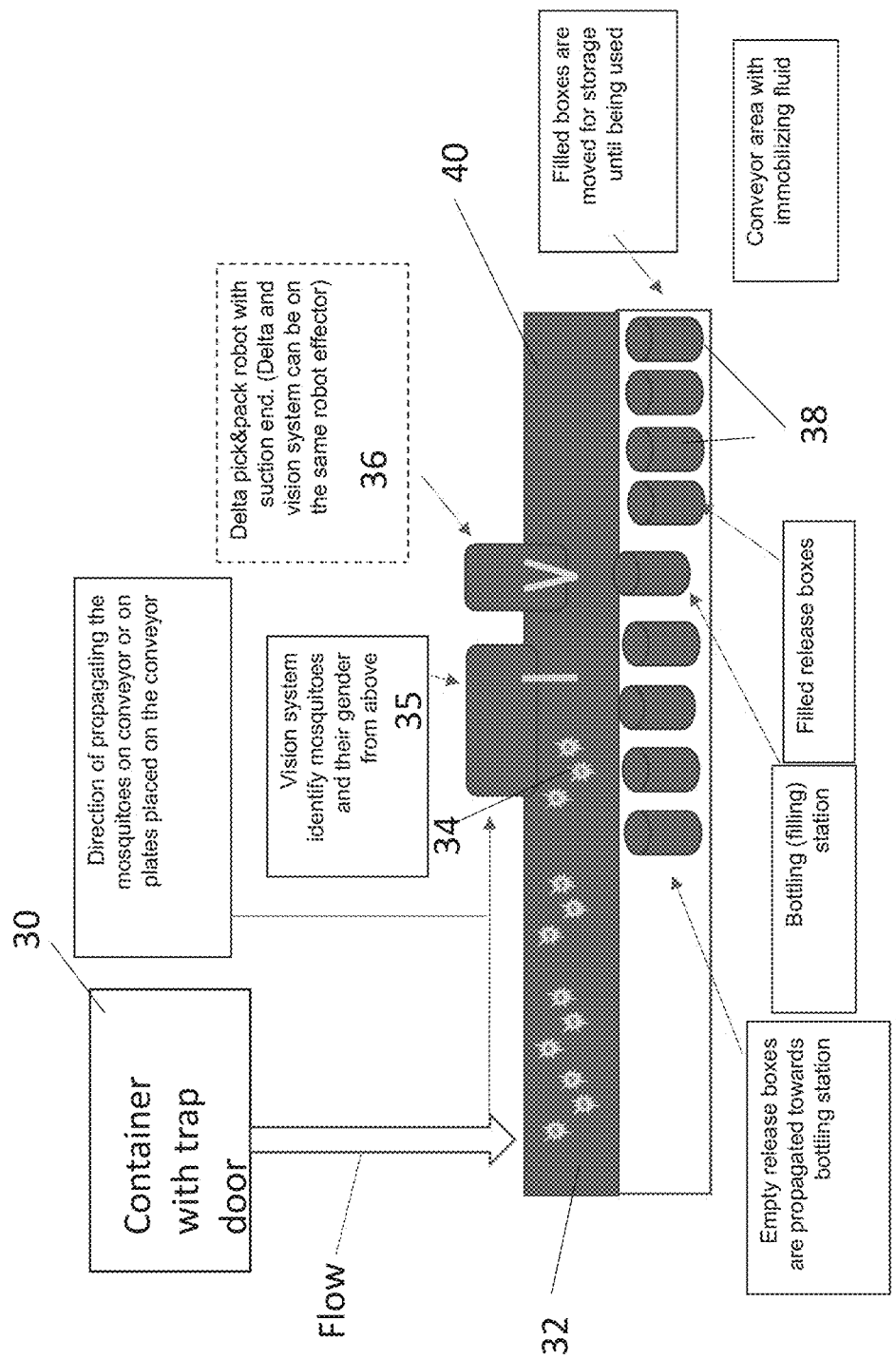

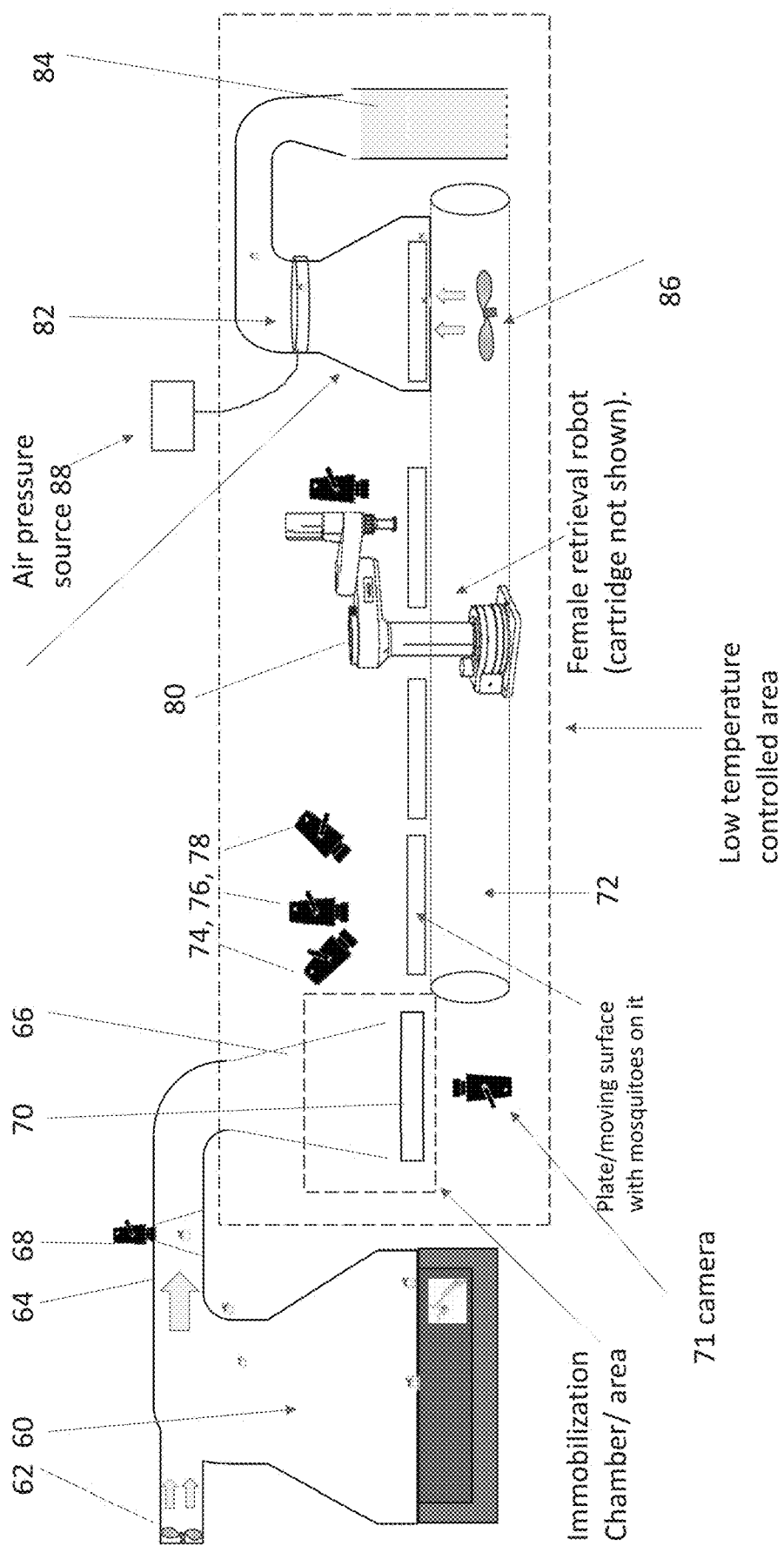

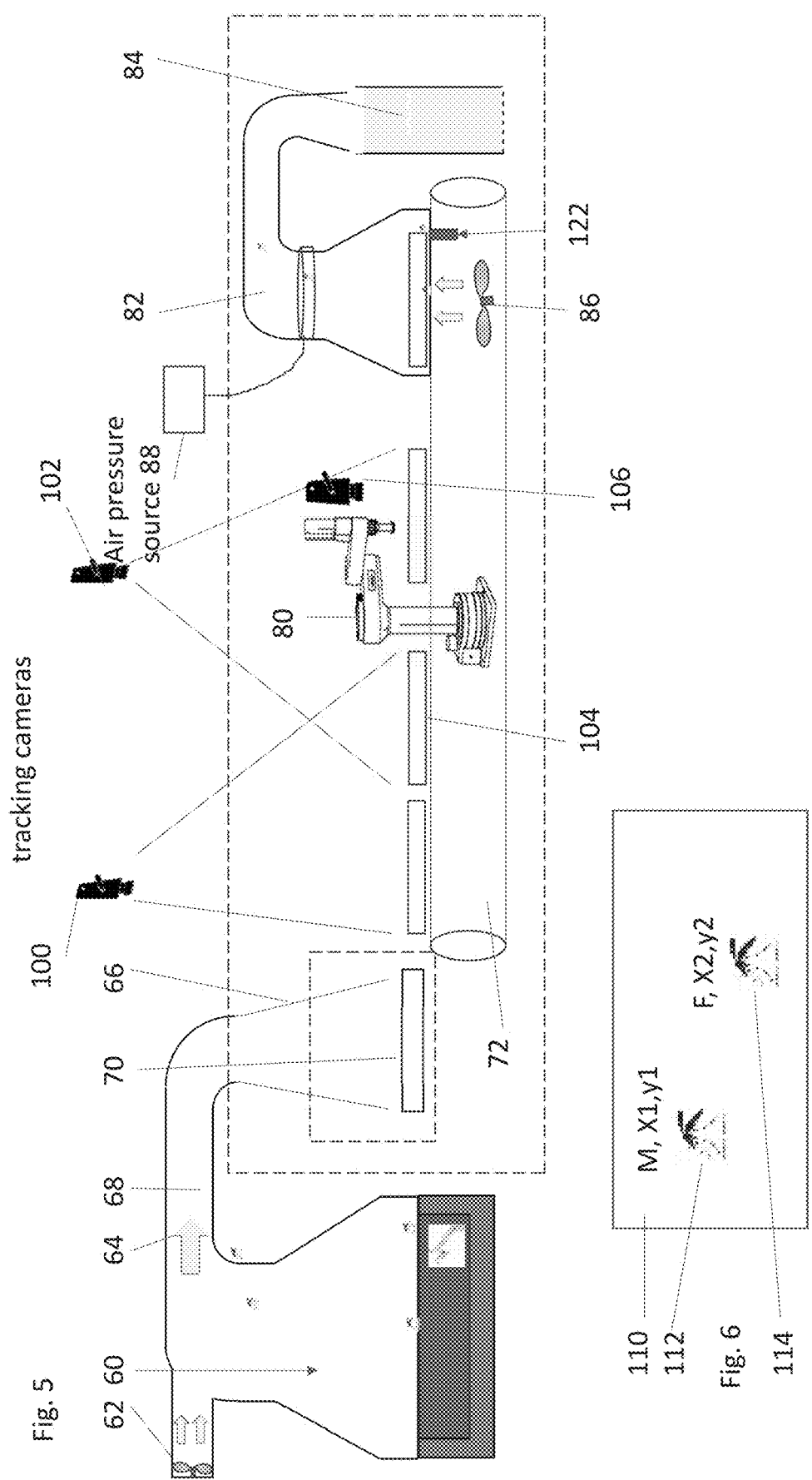

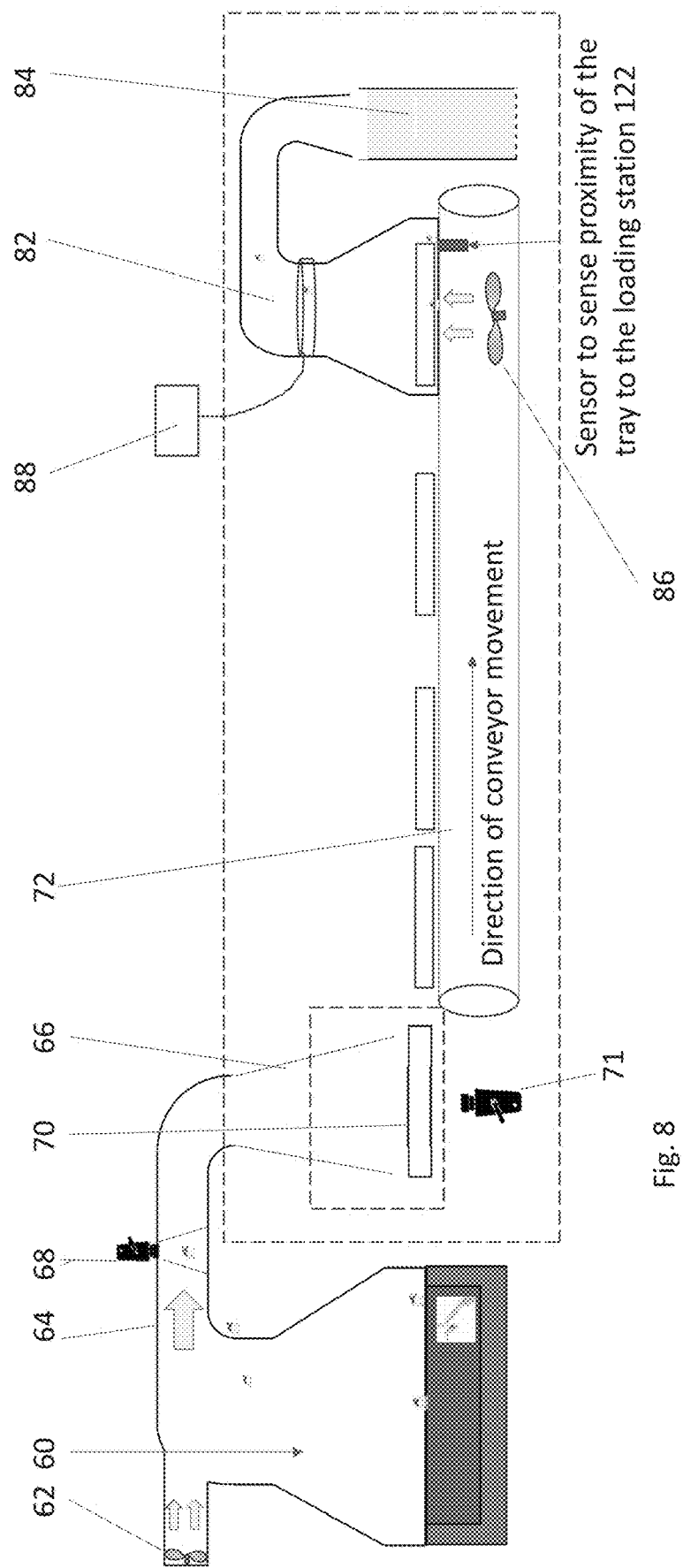

The plate with the enclosure moving on the conveying system

Rack of plates can be automatically loaded onto the conveying system, so the propelling (e.g pistons) system will move them towards the correct empty immobilization area preferably before a tray of pupa entered that hatching compartment.

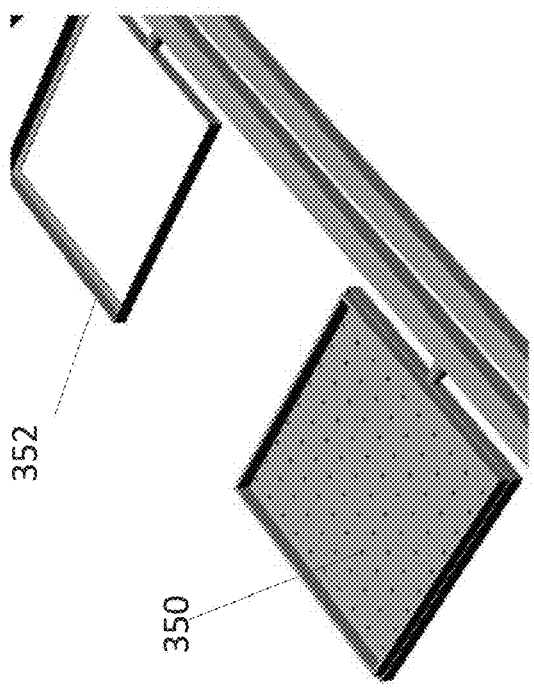
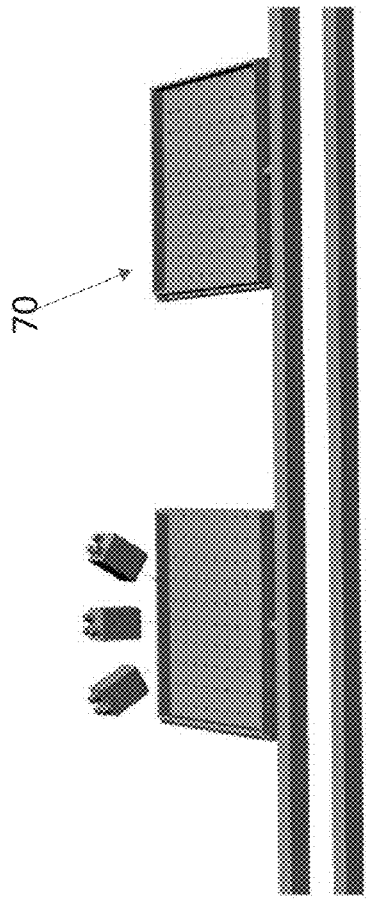
Fig. 34

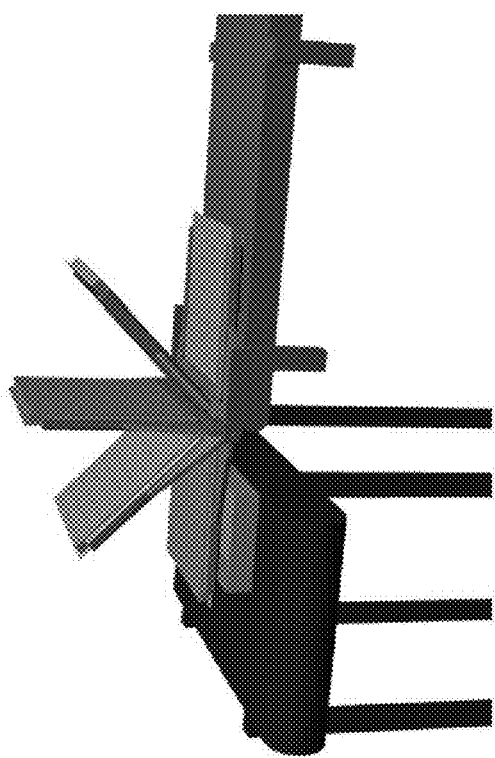
Fig. 39
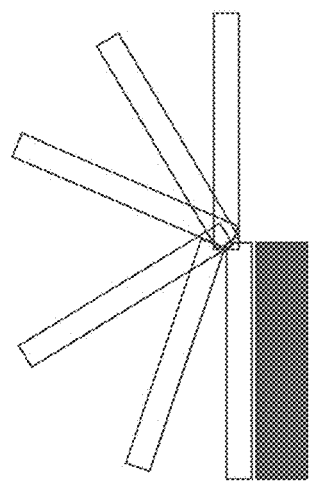
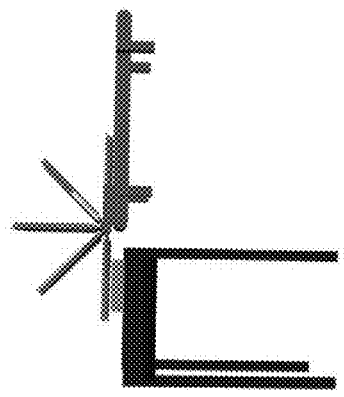

METHOD AND APPARATUS FOR SEX SORTING OF MOSQUITOES

RELATED APPLICATIONS

This application is a National Phase of PCT Patent Application No. PCT/IL2018/050738 having International filing date of Jul. 6, 2018, which claims the benefit of priority under 35 USC § 119(e) of U.S. Provisional Patent Application Nos. 62/668,842 filed on May 9, 2018, 62/647, 934 filed on Mar. 26, 2018, 62/533,242 filed on Jul. 17, 2017 and 62/529,057 filed on Jul. 6, 2017. The contents of the above applications are all incorporated by reference as if fully set forth herein in their entirety.

FIELD AND BACKGROUND OF THE INVENTION

The present invention, in some embodiments thereof, relates to sex sorting of mosquitoes and, more particularly, but not exclusively, to a method and apparatus for providing sorted male mosquitoes.

To date, mosquito SIT (Sterile Insect Technique) has proved itself in small scale projects around the globe, as a promising and effective tool for fighting mosquito-borne diseases. The idea is to release male mosquitoes with unique characteristics such that their offspring do not evolve, or the distributed males are sterile such that there will not be any offspring.

Small scale pilots, in which a few million male mosquitoes were released over a small area, have been carried out by different research institutions and companies, all demonstrating a reduction in mosquito population in that area weeks after deploying the engineered male mosquitoes on a weekly basis.

In order to treat large areas, millions of mosquitoes are needed to be produced on a daily basis.

However, the operational costs associated with the labor intensive activities involved in the rearing and handling process today prevent the mosquito SIT from scaling up. The specific steps in the rearing process comprise:

1. The sex sorting procedure. It is required to release males only, as opposed to releasing females when the target goal is to replace the local population and create a new type of mosquito population. The mosquitoes need to be sorted between females and males, and only males should be in the release boxes sent to the field for release.
2. The loading of the mosquitoes into the release boxes. Today, the common procedure is to place pupa (together with water) inside the release boxes. As each release box may contain in the order of 700-1500 mosquitoes, the workers need to transfer the pupa from other larger containers, and measure the quantity transferred, although resolution to a single mosquito is not required. Transferring 1,000 pupa into a release box at a time when millions of pupa per day are needed is highly intensive work requiring time and people. The costs are too high for large scale operations.

There is on-going research to optimize the sorting process. However, most systems to date, have tried to sort while in the pupa stage (based on weight, size, color). Other attempts have involved zapping the female mosquitoes while they are adults.

A problem is that the adult mosquito can be very active, and thus from the moment you classify its sex until you manage to do something it may have moved or flown away. Also having other mosquitoes in the field of view may obscure any vision sensor being used. Sorting at the pupa stage may lead to large collateral damage (meaning many dead males).

SUMMARY OF THE INVENTION

The present embodiments may use a time when adult mosquitoes are still, in order to apply imaging and then pick the wanted insects or zap the unwanted insects. Such a time may be the time when the insect emerges from the pupa, or when the insects are cooled down to a temperature at which they are still. In both cases the insects are still for a period of time which is long enough to be identified by the imaging process and then either picked up or zapped as the imaging process is able to guide a robot arm to find the insect.

According to an aspect of some embodiments of the present invention there is provided a method of providing insects for classifying insects for sorting into classes or for quality control of sorted insects, the method comprising:

providing the insects in a container having a closable opening;

opening the closable opening;

releasing the insects through the closable opening onto an air flow into a funnel, the air flow and the funnel carrying the insects to a collection location, the insects being collected on a conveyable surface;

applying immobilizing agent to the insects on the collection location, thereby to provide stationary insects for said sorting or quality control; and the insects being conveyed on said conveyable surface from said collection location.

In an embodiment, said immobilizing agent is one member of the group consisting of chilled air, carbon dioxide and ammonia, and an agent applied to said collection surface.

In an embodiment, the immobilizing agent is released into said funnel to provide a confined area of immobility, and said collection location is on a moving conveyor, the confined area being openable to allow conveying of said insects therefrom.

The method may involve providing multiple imaging locations around said conveyor to provide images of said immobilized insects for classification.

The method may involve providing overlap between said imaging locations to enable following of a given insect between different imaging locations.

The method may involve obtaining feature extractions from said imaging locations.

The method may involve obtaining classifications from each imaging location or from imaging locations and from extracted, and applying a rule to decide between different classifications of a same insect.

In an embodiment, the classifications are male and female, the method comprising retaining any insect for which all classifications are male.

According to a second aspect of the present invention there is provided a method of providing insects for sorting into classes comprising:

providing the insects from a robot arm;

placing each insect from said robot arm in a pattern onto a predetermined location on a moving conveyor;

continuing to place insects until said pattern is complete; and applying immobilizing agent to the insects on the conveyor; and conveying the insects, thereby to provide a flow of stationary insects for sorting.

In embodiments, said predetermined location is on a collection plate large enough to take a plurality of insects, the method comprising continuing to place insects until said plate is full and then moving said conveyor.

In an embodiment, said pattern is placed on a conveyable surface.

In an embodiment, the conveyable surface is porous, the method comprising setting up a pressure gradient across the plate.

In an embodiment, said immobilizing agent is one member of the group consisting of chilled air, carbon dioxide and ammonia and fluid applied to said conveyable surface.

In an embodiment, the immobilizing agent is released into a confined area of immobility on said moving conveyor, said confined area being opened to allow said conveying.

Embodiments may comprise providing multiple imaging locations around said conveyor to provide images of said immobilized insects for classification, and/or providing overlap between said imaging locations to enable following of a given insect between different imaging locations.

In an embodiment, said conveyor comprises a plurality of conveying sections.

In an embodiment, one of said classes is desired, and the method may comprise using a robot arm with a venturi ring for picking up insects of said desired class.

Embodiments may use suction with said venturi ring, said suction being continually operated and a valve being closed between picking up individual lots of insects.

Embodiments may provide a feeding station along said moving conveyor for feeding said insects.

In an embodiment, said feeding station is substantially free of said immobilizing agent, thereby to enable said insects to feed.

In an embodiment, said immobilizing agent is cold air, said conveyor or said conveying surface being kept at or below six degrees and said feeding area being kept at above six degrees.

Embodiments may comprise drawing the insects to said collection surface and inverting said collection surface.

According to a third aspect of the present invention there is provided apparatus for maturation of mosquitoes, comprising an egg tray for mosquitoes to lay eggs in, the egg tray being controllably fillable with water to reach a level at which eggs have been laid and a controllable drainage pipe to drain eggs or larvae, wherein the egg tray is coated with a non-stick surface.

In an embodiment, said egg tray drains into a larva tray, the larva tray sized to allow active swimming and feeding of insect larvae underwater.

In an embodiment, said larva tray or said egg tray is controllably drainable into a pupa tray, the pupa tray designed for pupa to float on a surface thereof and arranged for collection of emerging adults.

Embodiments may comprise imaging cameras for imaging, results of said imaging being used to control said filling or said draining.

A chute may be used for pouring said pupae, said chute being at least partly transparent to allow imaging by said cameras.

In an embodiment, the chute is widthwise extended, rows of pupae being formed in said chute according to size, the apparatus comprising at least one stopper under control of said imaging cameras for intervening between said rows to allow pupae from different rows to be separated.

According to a fourth aspect of the present invention there is provided apparatus for maturation of mosquitoes, comprising an egg tray for mosquitoes to lay eggs in, the egg tray being controllably fillable with water to reach a level at which eggs have been laid and a controllable drainage pipe to drain eggs or larvae into a second tray, the second tray having a lower capacity than said egg tray, the second tray having an upper sink hole to allow excess water to drain therefrom.

A pupa tray conveyor may be provided for conveying pupa trays to an emergence location.

According to a fifth aspect of the present invention there is provided a method of classifying adult mosquitoes into male and female mosquitoes, comprising:

obtaining a plurality of adult mosquitoes;
immobilizing the mosquitoes while the mosquitoes are standing;
locating their forward body parts;
imaging their forward body parts,
from the imaging identifying the antenna, the maxillary palp, and the proboscis;
identifying a male from at least one of a bushy antenna, a longer maxillary palp and a longer proboscis; and
identifying a female from at least one of a smooth antenna, a shorter maxillary palp and a shorter proboscis.

According to a sixth aspect of the present invention there is provided apparatus for classifying insects for sorting into classes or for quality control of sorted insects, the method comprising:

providing the insects in a container having a closable opening;
opening the closable opening;
releasing the insects through the closable opening onto an air flow into a funnel, the air flow and the funnel carrying the insects to a collection location, the insects being collected on a conveyable surface;
applying immobilizing agent to the insects on the collection location, thereby to provide stationary insects for said sorting or quality control; and
the insects being conveyed on said conveyable surface from said collection location.

In embodiments, the conveyor path includes a feeding station, and the feeding station may use a net and paper impregnated with sugar water.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the imaging and directing of the robot arms in embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWING(S)

Some embodiments of the invention are herein described, by way of example only, with reference to the accompanying drawings and photographs. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 2 is a simplified diagram showing a mosquito streaming device to which the present embodiments may apply;

FIG. 4 is a simplified schematic illustration of a line for producing a supply of sorted mosquitoes, according to the present embodiments;

FIG. 5 is a simplified schematic illustration of another line for producing a supply of sorted mosquitoes, according to the present embodiments;

FIG. 6 is a simplified schematic illustration of another line for producing a supply of sorted mosquitoes, according to the present embodiments;

FIG. 8 is a simplified schematic illustration of yet another line for producing a supply of sorted mosquitoes, according to the present embodiments;

FIG. 11 is a simplified diagram showing a feeding station along a conveyor according to embodiments of the present invention;

Figure 30:
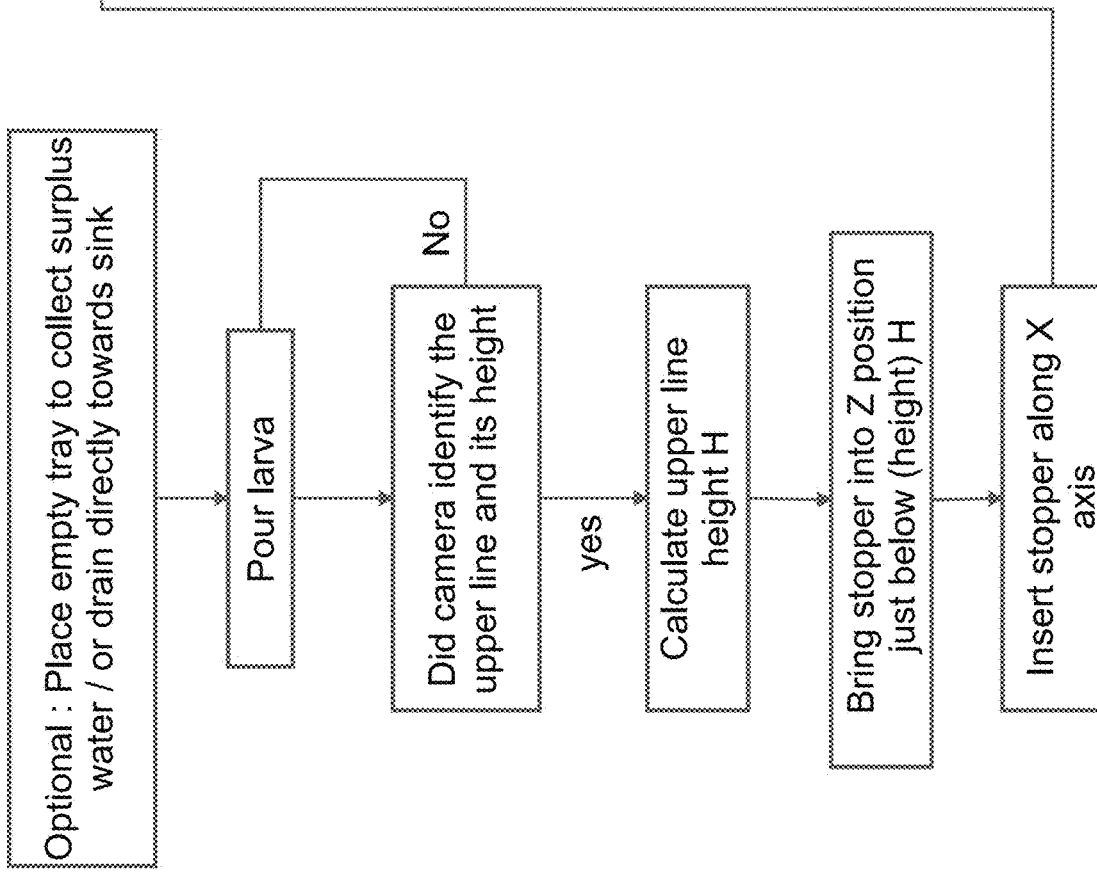
Figure 31:
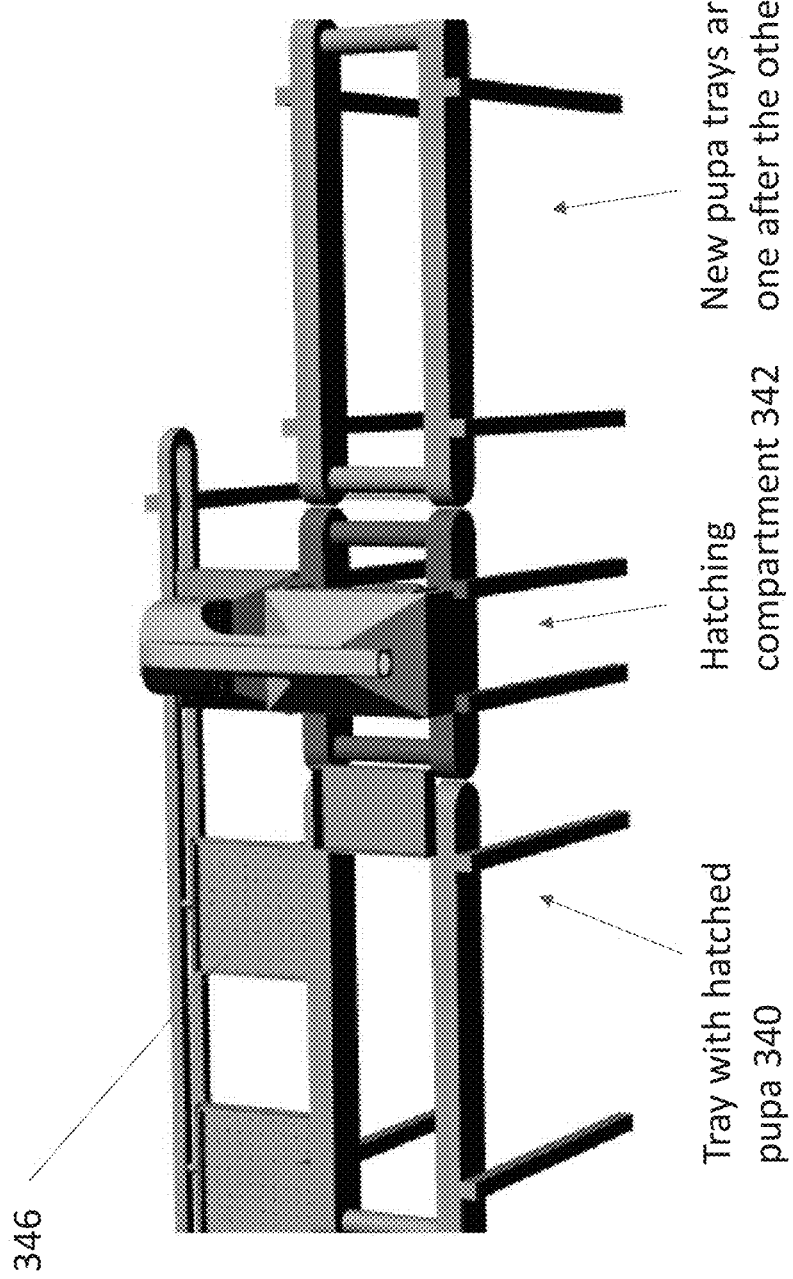
Figure 32:
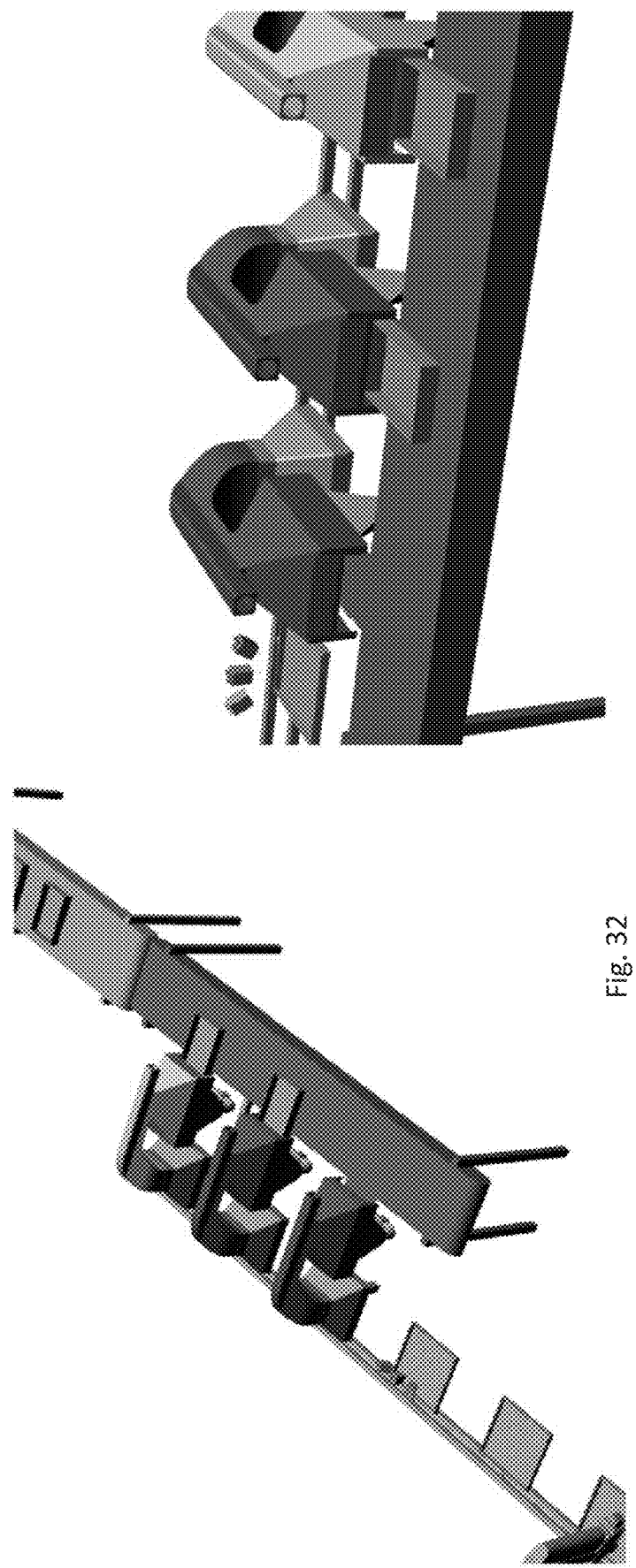
Figure 33:
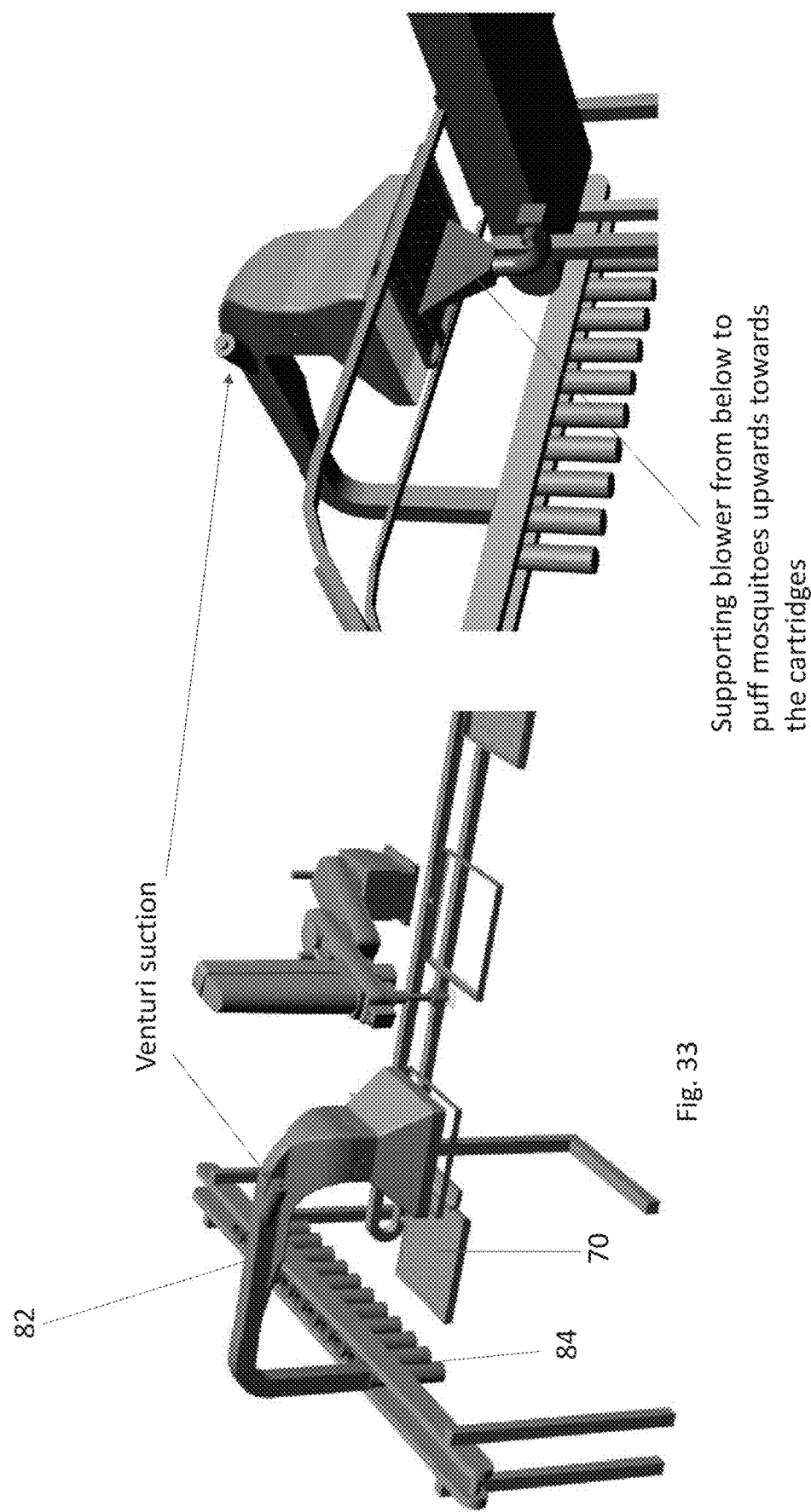

FIGS. 18, 19, 20, 21, 22A-B, 23, 24, 25, 26, 27, 28 and 29 are details of the mosquito growing and sorting apparatus, according to the present embodiments;

FIG. 30 is a flow chart illustrating egg hatching and larva and pupa management procedures based on draining water, according to the present embodiments;

FIGS. 31, 32 and 33 are details showing mechanical handling of pupa trays to manage emergence of the insects into a stream, according to the present embodiments;

FIG. 34 is a detail of a plate for handling of adult mosquitoes on a conveying apparatus; and FIGS. 35, 36, 37, 38 and 39 are details of plate handling on the conveyor.

DESCRIPTION OF SPECIFIC EMBODIMENTS OF THE INVENTION

The present invention, in some embodiments thereof, relates to sex sorting of mosquitoes and, more particularly, but not exclusively, to a method and apparatus for providing sorted male mosquitoes.

A method and apparatus for mechanical or electro-mechanical or other automatic sex-sorting of mosquitoes by extracting a class of mosquitoes from unsorted mosquitoes comprises obtaining unsorted mosquitoes, obtaining images of individual mosquitoes in a stationary phase, electronically classifying the individuals from the images into male mosquitoes and/or female mosquitoes, and possibly also unclassified objects; obtaining co-ordinates of individuals of at least one of the male mosquito and female mosquito classifications, and using a robot arm to reach an individual identified by the obtained coordinates to store or remove the individuals, thereby to provide sex-sorted mosquitoes.

The stationary phase is any phase in which the mosquito does not move or barely moves. One possibility is when the insects are cooled and remain motionless on walls, or cooled further to fall to the floor. Another possibility is when the adult insects emerge from the pupa.

It is to be noted herein that the terms "conveyor", "conveying" and other similar terms include any mode of transporting including using conveyor belts, pistons, motors, and robot arms.

The present embodiments relate to various aspects of hatching eggs, growing larvae and allowing adults to emerge from pupae, providing a stream of insects and classifying the stream into male and female, sorting the insects and packaging the desired class.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
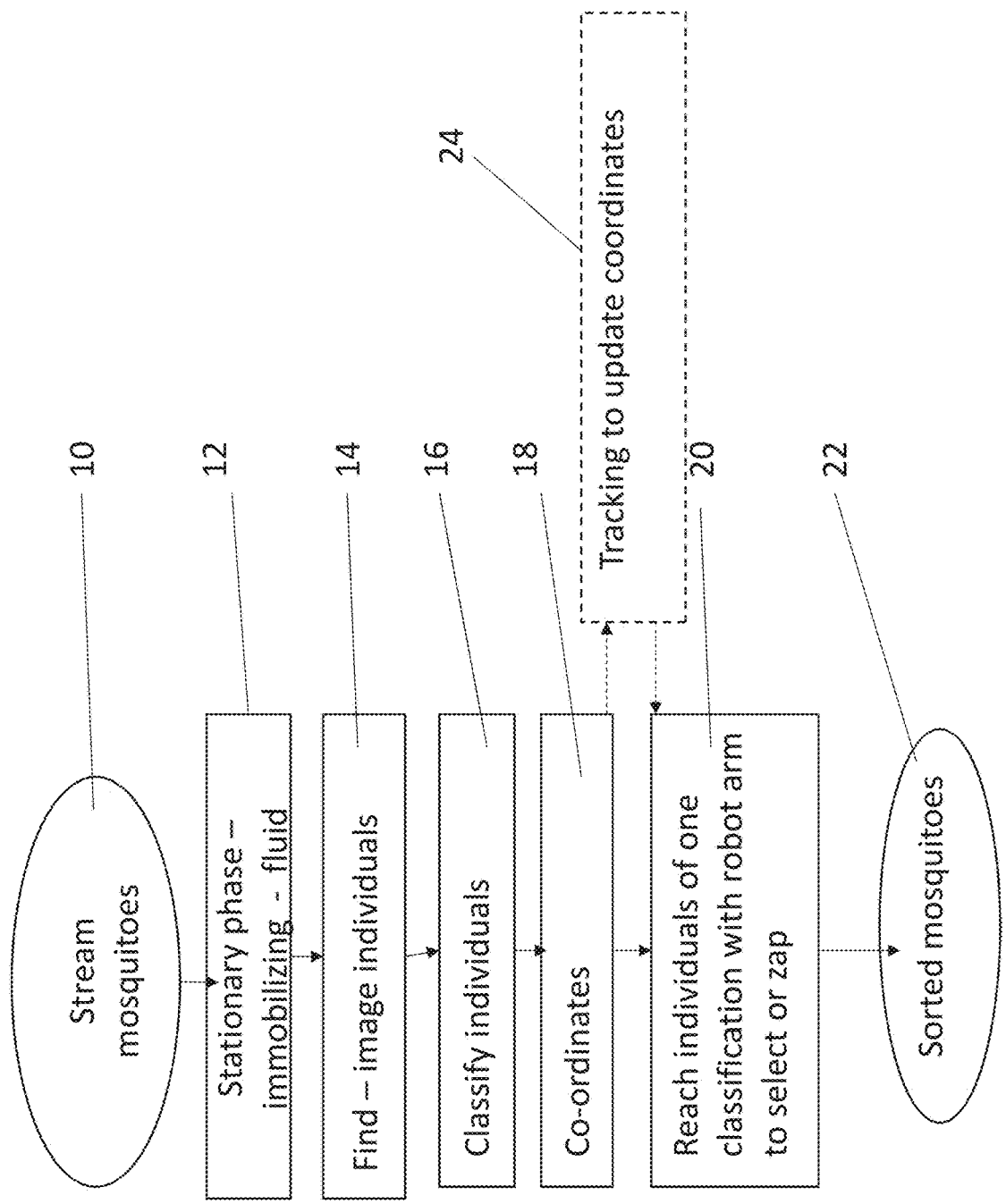
FIG. 1 is a simplified flow chart showing a procedure for providing and classifying a stream of mosquitoes, to which the present embodiments may apply.

Referring now to the drawings, FIG. 1 illustrates a flow chart showing a generalized procedure for providing and sorting mosquitoes on which some of the present embodiments are based. A method for mechanical sex-sorting of mosquitoes by extracting a class of mosquitoes from unsorted mosquitoes may begin with unsorted mosquitoes 10, which may be provided on an airstream. A stationary phase is caused, say applied using immobilizing fluid, for example cool air, in stage 12, and the mosquitoes are imaged in the stationary phase—14. The images are used 16 to classify the individuals. Classes used may include males and anything else, or females and anything else, or males, females and anything else. The coordinates are provided 18 alongside the gender of individuals of interest. In some cases the males are gathered, in other cases the females are removed. In other cases the insects have already been sorted, so that the imaging really relates to quality control. The insects in the stream may for example be expected all to be male, and females are regarded as contaminants, and the end result may be a count of the purity of the sample.

In the unsorted example, a robot arm may be used to reach an individual identified by the obtained coordinates to store or remove said individuals, thereby to provide sex-sorted mosquitoes 22.

Classifying may be carried out using a trained neural network, and the neural network may be a classical neural network or a deep network, including a convolutional neural network, or any other kind of neural network.

The trained neural network may comprise four or more layers.

In an embodiment, the stage of obtaining images 14 may relate to obtaining and considering single frames. Alternatively, successive frames may be classified together by generating differences between successive frames and using the differences to determine which individuals are in the stationary phase. Thus if successive frames difference over threshold show connected component with attributes like a mosquito, say size and gradients, the implication is that a stationary mosquito is being viewed.

Successive frame classifying may involve using a recurrent neural network (RNN), as will be discussed in greater detail below.

In an embodiment, the unsorted insects are emerging pupae and the stationary phase at 12 is the emergence phase in which the adult emerges from the pupa, and occurs prior to streaming 10. In a further alternative, the insects are sorted at emergence, so that streaming is of sorted insects, and then the imaging and classifying stage is a check to determine the purity of the sample.

The insects are not necessarily absolutely stationary during the stationary phase, and thus an embodiment uses imaging to track 24 movement of individual insects to update the coordinates obtained in box 18, so that the robot arm moves to the correct location. Multiple cameras may be present, and may have overlapping fields of view so that the same insect may be visible to multiple cameras at the same time, allowing for a handover procedure to pass on the following of a particular insect from one camera to another.

Obtaining images for classification may use a first, relatively high resolution, camera, and tracking may use a second, relatively low resolution, camera with a wide field of view.

Alternatively individual cameras may be used for both purposes, and the cameras may combine sufficient resolution with relatively large field of view.

In embodiments, the obtained coordinates are of the male class and the identified individuals are picked off and placed in storage or packed in cartridges. The robot arm may use a suction device or a blower device to pick off the identified individuals and place them in storage.

Alternatively, the obtained coordinates are of the female class and the identified individuals are destroyed or otherwise disposed of. A small number may be retained for breeding. The robot arm may comprise a zapper for destroying the identified individuals, or may as before use a suction device or blower.

The zapper may be an electrode or a solenoid or a laser etc.

In an embodiment, if an individual is not classified into male or female by a predetermined time, then the image is sent to an operator for adjudication. Alternatively, if an individual is not classified as male by a predetermined time then it is classified as female. As will be discussed in greater detail below, different cameras giving different points of view, or different image features, may be given votes. Thus one camera or feature may indicate male and one female, or both male or both female. If what is required is to collect males only with as little error as possible then one solution is to retain only those insects getting a vote of male from all participants and discarding all the rest.

In an embodiment, the insects are cooled for imaging in a container having walls, so that the cooled insects stand on an interior side of the walls. Then the box is dismantled to present the interior sides of the walls for imaging. In a further embodiment a region of confinement is constructed around a conveyor and immobilizing fluid is blown into the region of confinement along with the insects, which thus arrive motionless on the conveyor.

Referring now to FIG. 2, the insects are cooled in a container 30 having a closable opening, for example using a trap door, and the trap door is opened onto a first moving conveyor 32. In an embodiment the conveyor is held at low temperature to immobilize the insects once they land on the conveyor. In another embodiment cool air or $CO_2$ or other immobilizing fluid is added to the stream to allow the cooled insects to fall onto the conveyor. The first moving conveyor carries the insects to an imaging location 34 under camera-imaging system 35. Imaging system 35 may include multiple cameras to view the insects from different angles and at different locations. The conveyor in some embodiments may stop when insects reach the imaging location to allow for imaging with coordinates. In other embodiments, images are taken as the conveyor moves and insects are tracked from one location to another. Finally, robot 36 picks the selected insects, in this case generally the females, leaving the males to fall off the end of the conveyor into release boxes 38. In other embodiments the insects picked off may be the males, which are picked off to be packaged. In yet further embodiments, imaging is simply used to determine the purity of the sample. If the purity is above a certain threshold then the insects are packed and used and if not then the insects are discarded. In a yet further embodiment, if contaminating insects are detected, they may be removed, either automatically or by operator intervention. In this case the operator would be shown that a contaminating insect is present and can operate the robot. The operator sees how pure the sample is and can decide whether it is worth purifying or whether the current sample should simply be discarded.

In an embodiment, the part 40 of conveyor 32 beyond the imaging area may be a second conveyor which collects mosquitoes from the first conveyor and then travels more slowly to the filling area. In general, conveyors may be split into part conveyors with junctions in between and an overall system can be built up having numerous supply points, packing locations and imaging locations. The system is thus scalable for production of the required number of insects.

The first moving conveyor 32 may be a relatively fast moving conveyor, where the speed spreads out the falling mosquitoes, so that the insects don't pile and disrupt imaging. The first moving conveyor 32 may empty onto second moving conveyor 40, being a relatively slow moving conveyor.

In greater detail, the present embodiments provide technology for automatic or semi-automatic detection and classification of mosquitoes.

In order to be able to perform a good classification and selection of the mosquitos, the identified mosquito needs to be in a position where it can be identified as an individual and seen clearly, and then it should stay relatively still and certainly not fly away between classification and the time at which it can be picked or removed in the sorting process.

Two different embodiments provide these properties in different ways.

A first embodiment uses cooling to cool down the air, so that the mosquitoes do not move and then it makes the classification. In embodiments, the temperature is lowered to ~6-12 degree Celsius, low enough so that the mosquitoes do not fly, but high enough so they continue standing, and not falling on the floor and getting tangled with one another.

A variation of the same embodiment lowers the temperature further, or the cage is shaken with the previous level of cooling, so as knock the mosquitoes down on the floor.

A second embodiment uses a system that monitors a tray of pupae at around the stage of emergence, and utilizes the fact that the mosquito sex can already be visually identified just before the adult mosquito is fully emerged. At this point the mosquito is stationary or almost stationary for several minutes, providing sufficient time to detect, classify and then carry out selection. Such a system is made of a pupa tray with water, pupa and a vision system. As will be discussed, different methods of image classification are suitable for different embodiments, and these include both classical neural networks and convolutional and other networks involving deep learning.

The present embodiments, may automatically sort and handle the adult insects based on the classification process to provide sorted insects in release cartridges.

The present embodiments may either handle the males for selection and further use, leaving the females behind, or handle the females and remove them, leaving the males for further use.

The robotic system may potentially receive a priority list from the detection and classification system, instructing it which mosquito to handle first, as will be described in greater detail below.

An embodiment may include a pupa tray with water and pupa inside.

There may be further provided a vision sensor to detect and classify the mosquitoes upon their emergence.

Optionally a cage with nets surrounding the pupa tray in order to prevent any emerging mosquitoes from escaping to the outside.

A robotic system may contain an arm and a handling tool for handling the individual mosquitoes. The robotic system also includes a controller to receive coordinates and guide the robotic arm and handling tool to move to those coordinates. The movements may be on X-Y-Z axis, providing the ability for the handling tool to reach all areas in front of the surface on which the adult mosquitoes are standing.

In one embodiment, the handling tool may comprise a suction tube and a motor with controller. Suction may be in the order of 3-8 meters per second for a tube diameter in the order of 6-12 mm. Larger tubes are possible but may suck more than just the selected target mosquito, thus upsetting the selection ability of the system.

The handling tool travels to the mosquito X-Y position, and the suction tube is lowered along the Z axis to meet the mosquito.

The vision system is placed at a distance that provides the required resolution for the sensor, be it just above the pupa dish, or above the cage with a transparent roof top and zoom-in capability.

Typical camera resolution may be 5 MegaPixels, that is using a sensor of 2000×2500 pixels. If the field of view is a region having a length of 30 cm, you divide by the dimension and get the number of pixels per mm. The present embodiments may have at least two to three pixels along the length of the distinguishing features of the mosquitoes. The distance of the camera from the tray and the number of pixels on the sensor are thus connected to provide a sensitivity.

A vision system such as a camera, controller unit and software, may acquire a sequence of continuous frames of the mosquito in order to detect classify and/or track its position.

Since the mosquito can be oriented in different ways, with some visual noise in the background, embodiments may use a deep learning approach based on convolutional neural networks to detect and classify the mosquito sex.

In another embodiment, pre-processing of the image may be carried out using methods from classical image processing, such as obtaining outlines etc. Then the deep learning is provided with the processed results.

The vision module may processes each of a plurality of frames taken separately and independently. Alternatively the succeeding frames can be used together to make available a sequential form of the problem, and treat the input as a video. However it is generally believed that for video processing, wrapping a single image processing module in a recurrent neural network (RNN) architecture may gain better results.

The present embodiments may contain one or two cameras above the tray of pupas in which tray it is expected that the adults are about to emerge any moment, A robot arm with a laser, or any other zapper may also be provided that may operate at the given mosquito coordinates according to a set of algorithms.

The set of algorithms may find where, in the image and in the physical world, there is an emergence of a mosquito from a pupa and may then track its location with time.

A high resolution camera, may look for the features of the mosquito that particularly identify the gender, such as the antenna area. In addition there may be a low resolution camera that is required for tracking. Alternatively, a single camera may provide both detection-classification and tracking, if the tracking area is covered within the camera field of view (FOV).

The inputs for imaging and location are: a continuous sequence of images from an upper projection of a tray with mosquitoes and pupae in water inside the tray.

A requirement may be:

"Finding the real world coordinates of all female mosquitoes in the captured tray at any given moment".

In that case the object will be classified either as female, or "other" (either male or pupa or other visual noise). This can be useful for quality control or when it is only needed to extract the females. It is possible to use the algorithm breakdown below and define a different purpose—"Finding the real world coordinates of all male mosquitoes in the captured tray at any given moment", or further to "find the real world coordinates of all male mosquitoes and female mosquitoes in the captured tray at any given moment".

For that purpose, we may use the following features:
1) Camera calibration (one time for system set-up, and as necessary during maintenance etc.)
2) Detect ROI's (region of interest) of each mosquito.
3) Classify gender of each mosquito
4) Prioritize mosquitoes
5) Track each classified female mosquito
6) Transform pixel coordinates system into real-world coordinates system Upon system set-up there is a camera calibration procedure in order to enable finding the transformation between the pixel's coordinates system and the physical coordinate system.

If the system consists of two cameras, e.g. high & low resolution as suggested above, then a calibration between each camera may be derived from the calibration parameters of each camera.

Camera calibration using a check-board or other patterns is known, and such known methods are provided as an example:

"A Flexible New Technique for Camera Calibration", Zhengyou Zhang, 1998, Microsoft (www(dot)microsoft(dot)com/en-us/research/publication/a-flexible-new-technique-for-camera-calibration/).

"A Four-step Camera Calibration Procedure with Implicit Image Correction", Janne Heikkilä and Olli Silvén, University of Oulu, Finland.

The implementation of the algorithm is common knowledge, and sample code is publicly available.

In camera calibration there is a model that is divided into extrinsic (orientation and location) and intrinsic (mainly optical) parameters. Having all of these parameters allows a transformation between the image coordinates system and the real-world coordinate system.

Calibration is done by capturing several pictures in various orientations of a checkerboard or other easy to detect pattern. By corresponding detection or marker points in each of the pictures, an optimization process may be converted to the correct camera model parameters.

Once we have the transformation parameters (intrinsic and extrinsic parameters) we can translate mosquito location to a physical location for the mechanical system to work.

Since the cameras are mechanically stable, the calibration process is done once (or for maintenance reasons every couple of months\years).

With two cameras, and having the transformation parameters for each camera we calculate the transformation between the two cameras' pixel coordinate systems. Then we can use coordinates from the high resolution camera and transform them into the low resolution camera for the tracking algorithm, and output them either for the mechanical zapper or pinpointing for a human operator where the classified mosquito is to be found.

An accuracy of the calibration is a system parameter that is used for the tracking algorithm and for the mechanical cannon.

The detection (the task of finding where the mosquitoes are in the image) and the classification (the task of determining which gender it is) may be jointly solved by any of the following algorithms as examples:

Single Shot MultiBox Detector (www(dot)arxiv(dot)org/abs/1512.02325 Authors: Wei Liu1, Dragomir Anguelov2, Dumitru Erhan3, Christian Szegedy3, Scott Reed4, Cheng-Yang Fu1, Alexander C. Berg1, UNC Chapel Hill 2Zoox Inc. 3Google Inc. 4University of Michigan, Ann-Arbor).

Faster rcnn: www(dot)arxiv(dot)org/abs/1506.01497 ("Faster R-CNN: Towards Real-Time Object Detection with Region Proposal Networks", authors: Shaoqing Ren, Kaiming He, Ross Girshick, and Jian Sun).

Yolo: www(dot)pjreddie(dot)com/media/files/papers/yolo(dot)pdf.

These kinds of algorithms may train a network that is a combination of an RPN (region proposal network) and a classification network that shares the same convolutional features. The RPN proposes various bounding boxes that contain an object with high probability and this way actually tells the classification network where to look in the image. The classification network may be trained to determine to which class the object belongs.

In the present embodiments, concerning detection-classification of mosquitoes, we may define the possible classes as male\female\none or only as female\none or only as male\none In order to train the network we may collect a large number of labeled pictures containing male and female mosquitos.

To train for only one class, female for example, we may provide the network with either male pictures or background pictures for the non-female class. This way the network may train to look for the relevant attributes of females and not general attributes of mosquitos that are common to males and females.

The background pictures may be empty water or pupas or mosquitoes whose gender cannot be determined yet.

The classification net in each of these algorithms may be changed and we may use transfer learning as fine tuning or as a feature vector, which may be done using nets such as Alexnet, VGG and Inception.

Transfer learning is described in those examples: "ImageNet Classification with Deep Convolutional Neural Networks", Alex Krizhevsky, Ilya Sutskever, Geoffrey E. Hinton (www(dot)papers(dot)nips(dot)cc/paper/4824-imagenet-classification-with-deep-convolutional-neural-networks(dot)pdf).

"VERY DEEP CONVOLUTIONAL NETWORKS FOR LARGE-SCALE IMAGE RECOGNITION" Karen Simonyan & Andrew Zisserman (www(dot)arxiv(dot)org/pdf/1409.1556v6(dot)pdf).

The output of the detection & classification for a single image is a list of rectangles (ROI's) and corresponding probabilities as to whether each of them is a female mosquito, or a general probability that the object belong to each of the classes. This output is a list of vectors $(X\_i, Y\_i, W\_i, H\_i, [P\_i\_1, \ldots P\_i\_n])$ where: I is ROI detected index and n is the number of classes:

$(X\_i, Y\_i)$=are coordinates in the image of where the detected ROI is $(W\_i, H\_i)$=are the width and height of the detected ROI, and $(P\_i\_1, P\_i\_2, \ldots P\_i\_n)$ is the list of probabilities of the object in the ROI to belong to each of the classes.

A possible network configuration may be an RNN (recurrent neural network) which is a network that store state and classify differently according to its current state.

The architecture we propose works on a single image. It is known that in video processing there is an advantage to using RNN architecture. In this way the continuity of the images taken before the mosquito fully appears affects the probability that it will be male or female. The accumulated additional knowledge from each frame increases the probability for positive classification.

Relevant methods:
www(dot)cv-foundation(dot)org/openaccess/content_cvpr_2015/papers/Ng_Beyond_Short_Snippets_2015_CVPR_paper(dot)pdf.
www(dot)static(dot)googleusercontent(dot)com/media/research.google(dot)com/en//pubs/archive/42455(dot)pdf.

A further implementation also uses previous frames to process a current frame and thus comes under the heading of using video as input.

In this implementation, since the camera is stable, and the pupas hardly moving, only areas of emergence change over adjacent frames. Thus we are able to detect the moment of emergence to be utilized for prioritization as will be discussed in greater detail below. Such knowledge can be used by adding a term to the loss function of the RPN that describes a delta between successive image frames, thus the L2 measure of images or of feature space. In other words the embodiment punishes results of detection where there is little variation and incentivize the RPN for detection results where there is high variation.

During the emergence phase there arises a point in time when the mosquito stops changing its form, which point may be confirmed against an average or maximum time from beginning to end of emergence, or from the moment either six legs of the mosquitoes are out of the pupa.

One method is to determine the time that the image ROI begins to change more rapidly, say using a threshold on adjacent image L2 deltas. The approach is feasible since the pupa images before the emergence process begins are stable, older pupa reaching the stage of emergence hardly move in water. The pupa trays may already be sorted and tagged according to date of pupation (transformation from larva to pupa).

A second method is to train the classification network to classify between more than two classes, namely male and female, and instead use four or more classes: young male, adult male, young female, and adult female. The young male or female classes are defined as those mosquitoes whose legs are not yet fully seen and adult males or females are those mosquitoes whose body is fully exposed. Using this method the number of classes can be extended to more than four for a finer distinguishing of different levels of emergence.

The system may store in memory all instances of emerged mosquitoes and their timing (according to above rule), and then provide the next mosquito to be handled according to a FIFO queue (first to emerge, first to be handled).

The training process of the neural networks is a process that may be carried out once using a large labeled database. There are many factors that affect good training: selecting activation functions, selecting optimization model, how to initialize the weights of the net, determine hyper-parameters, dropout, data augmentation and many more.

The result of a good training process is a set of final values of the weights of the neural networks, which can then be used to classify the images.

Using a trained network on the training database may give the time since the start of emergence that is required to arrive at a successful classification.

For example, the average number of frames (given a constant frame rate) from the start of emergence until the gender classification may be known with 90% probability to be 250 frames (at a rate of 2 frames per second). This information, which may be collected during the training process, may serve the robotic system afterwards to know how much time remains to operate on the classified mosquito.

A mosquito may travel on the surface and tracking is suggested to provide correct coordinates for the operator/robotic handling tool.

Tracking algorithms exploit information of a movement model that contains common velocities and accelerations, to punish\incentivize possible locations of the target in the next frame. Using tracking, partial occlusion or error on the target detection can be compensated.

Tracking parameters for the tracking algorithm may include:
Average/maximal velocity of mosquitos;
Average/maximal acceleration of mosquitoes;
Average/maximal of movement duration;
Angular velocity of movement;
Angular acceleration of movement;
Camera parameters, such as focal length, distance of camera from tray, camera orientation) for translate all spatial units to pixel units; and
Camera exposure time to avoid blurring of a moving object.

An existing tracking algorithms that may be used is a Kalman filter based tracking algorithm.

A vision sensor may capture frames from the tray and a deep learning algorithm uses the frame to detect-classify an emerging mosquito. Then the tracking algorithm tracks the mosquito if it moves. Then optionally the coordinates may be sent to an operator in the semi-automatic process, or tracked coordinates may be sent to a robotic system to carry out suction of the mosquito or killing the mosquito with a laser beam or other means.

An alternative embodiment may work on insects as they are warmed and slowly become active. The embodiment may involve cooling of the air where the mosquitoes are stored to a temperature of 6-12 degrees, so that the mosquitoes are resting, almost not moving, but not falling on the ground. Alternatively, the temperature may be set to lower than 6 degrees, so that the mosquitoes are motionless on the floor.

The vision sensor then operates on the cage or plate with the cold and motionless mosquitoes. As in the previous embodiment, a vision algorithm which may be based on deep learning may detect-classify the mosquitoes. If the temperature is above six degrees then tracking may be needed as the mosquitoes do move somewhat. At temperatures below six degrees there is no motion and tracking is not needed.

If training only one class (female for example) one may provide the network either male pictures or background pictures to the non-female class. This way the network may train to look for the relevant attributes of females and not general attributes of mosquitos that are common to males and females. This may create a more efficient network.

An embodiment may run two networks in parallel on the same frames—one that classifies only females, and a second that classifies only males.

As mentioned above, instead of working on individual frames, using video may have an advantage.

If using video then a possible network configuration is RNN (recurrent neural network) which is a network that stores a state and classifies differently according to its current state. The continuity of the images taken before the mosquito fully appears affects the probability that it will be male or female. The accumulated additional knowledge from each frame increases the probability for positive classification.

The system may be able to identify, that is detect the emerging mosquito and where it lies in the emergence process, that is the system may identify the point in time when a mosquito is first fully emerged. Metrics that may be used include average time from start of emergence. Alternatively visual classification of parts of the emergence process may be used. The results are used to enter the current emerging mosquito into a queue for the robotic system, which the robotic system may then deal with in order.

For scaling the detecting and sorting process to large quantities, an automated system may continuously feed the vision system with mosquitoes, however the mosquitoes should be in a state in which they can be clearly imaged. Thus the mosquitoes should be separated from each other, or at least not one on top of the other, so that vision system is able to identify the unique gender features of individual mosquitoes and provide an answer as to whether the object is a mosquito and then if it is a male or female mosquito.

However, in order to increase the yield of the system, large numbers of mosquitoes may pass through the vision system per unit time.

In the following we provide two embodiments for a continuous feed of mosquitoes without piling one on top of the other.

A first embodiment comprises:
a. A cooling system;
b. Mosquito storage compartments;
c. Conveyance mechanism to move mosquitoes forward;
d. Vision system with controller. The controller may be connected to the conveyor to stop when required and to provide coordinates;
e. Pick and place robot to suck or blow. For example it may include a common suction pipette or electric air pump or a blower which can be used either for blowing or in reverse as a suction device. The robot may puff male or female mosquitoes.

Alternatively a zapper such as a laser beam may puncture or extract female mosquitoes in any other way which kills them.

In the embodiment the temperature is lowered so that the mosquitoes fall onto the floor below. However the floor is moving, since the floor is a moving conveyor, and thus no piling up occurs.

In embodiments, if the vision system is unable to classify the mosquito as a female or male, it may send the image to an operator, who may carry out the classification. Other embodiments may zap unidentified mosquitoes along with the females.

In embodiments, the insects may be provided for sorting into classes or the insects may already be sorted, the samples requiring quality control to find any contamination of the sample by the unwanted class.

Figure 3C:
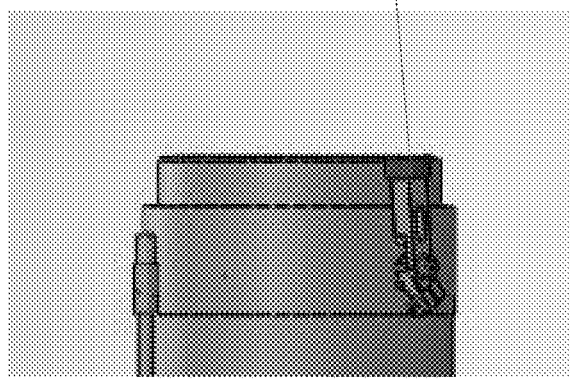
FIGS. 3A-3C are three views of a container with actuated openings at both ends that may be used in the present embodiments.
Figure 3B:
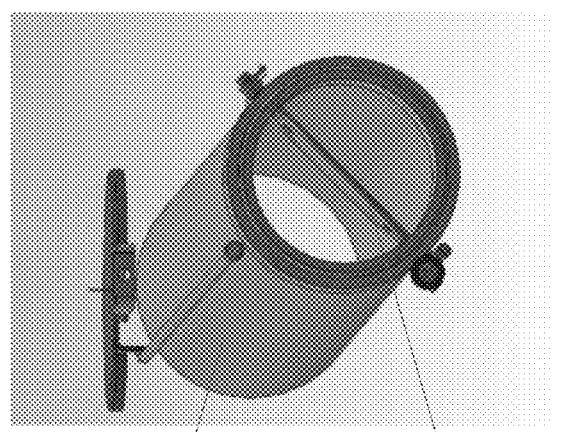
Figure 3A:
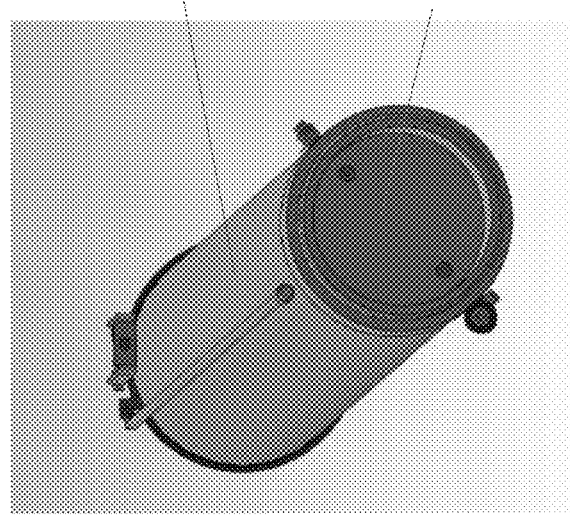

The insects may be provided in a container having a closable opening, such as that shown in FIGS. 3A . . . 3C. FIG. 3A shows the container 50 with door 52 closed. FIG. 3B shows the container 50 open at both ends, with door 52 rotated. FIG. 3C shows a detail of an exemplary closing mechanism for container 50. Magnet 54 is connected to the door. An opening mechanism passes by and pushes back the magnet 54, which releases door 52.

The closing mechanism may enable the door to be opened while a loading element is close to the opening, and then the door may be automatically closed as the loading element moves away. The insects are released into a stream of air, typically blowing through the container, and they are carried by the airstream towards a landing point, which serves as a collection area. The collection area may be the surface of a conveyor belt which is moving. The collection area may be a plate on the conveyor, or a plate that is moved in some other way, say with pistons.

The plate may be glass. Alternatively, Surface plates may have holes letting air go through them, while being small enough the insect won't fall through. Surfaces may be also attached in a way to a conveyor that enables flipping the plate over or vibrating of the surface. Flipping of the plate allows for emptying of the plate into a container without needing suction.

Negative pressure may be applied behind the collection area, so that the air current doesn't get too turbulent around the collection area. Immobilizing agent, say cool air, or carbon dioxide or ammonia, may be applied to the insects in the airflow, to immobilize the insects prior to landing, or the landing area may be cooled, to immobilize the insects once they have landed.

As explained, in one embodiment, the wanted class of insects is collected. In another embodiment the unwanted class of insects is collected and the remainder are left on the conveyor for packaging. If the insects are already sorted then classifying may carried out for quality control. Identified contaminants may be removed, or the number of contaminants may be counted, and if reaching a threshold, the entire batch may be discarded. In borderline cases, coordinates of the contaminating insects may be provided to allow an operator to decide whether the batch is worth saving.

Then if the quality control threshold is met, then the entire batch is simply packaged as is.

Reference is now made to FIG. 4, which illustrates an insect source 60, an air pressure source 62 to drive insects into an airstream through tube 64 and funnel 66, passed camera 68 and onto collection area 70, here a plate. Camera 71 views from below the plate. The plate moves on a propulsion system 72 passed cameras 74, 76 and 78 at different angles, past female collection arm 80 and on to general collection arm 82, which collects the wanted insects, here males, into collection flask 84.

Funnel 66 is for guidance of the air stream. The funnel may be connected to a drive system, such as a linear rail with servo motor, to enable lowering and raising the funnel exactly above the mosquito plate at collection area 70, based say on sensing the location of the plate.

Camera 71 may be fore object coordinate detection, to count the number of insects on the plate and thus to trigger removal of the plate when full and replacement with a fresh plate.

General collection arm 82 may be a suction or other air flow device, as an example a Bernoulli suction ring is depicted, for creating suction flow to lift the mosquitos and guide them towards the collection flask 84. Air pressure sources 86 may provide an air draught and air pressure source 88 from above may apply the Bernoulli effect in a venturi ring. The suction may be continually operated during the sorting process, and a valve may be closed between picking up individual lots of insects.

In order to be imaged effectively, the insects should be upright and not bunched together. The use of an airstream rather than just pouring the insects from the container may help. In addition, the collection site may be moving as the insects are dispensed. In addition the landing area may be vibrated to stop insects piling on top of each other. Another way of getting the insects to separate may comprise warming the collection area slightly so that the insects move off each other.

Immobilizing agent may be released into a confined area of immobility on the moving conveyor, for example a demarcated region formed by funnel walls that funnel the insects from the release point to the collection point. The immobilization fluid may also be concentrated within the funnel area.

As an alternative to immobilization fluid, the collection area, say a sample plate or conveyor belt, may be electronically cooled. For example peltier cooling units may be used.

The conveying mechanism 72 may be a conveyor belt and in embodiments may provide a cooling surface. In embodiments the immobilization area may be along the conveyor and may be divided into two or more separate areas. The insects arrive at the first area, and when the first area is full they then move on to the second and subsequent areas for classifying, sorting, feeding and the like.

The vision system 35 may be made up of cameras 68, 71, 74, 76, 78, at multiple imaging locations around the conveyor to provide images of the immobilized insects from different angles and to overlap between images. Reference is made to FIG. 5 which shows two cameras 100 and 102 and overlap area 104 between their fields of view. Overlap between the cameras may enable following of a given insect between different imaging locations, so that say a particular insect may be classified and then followed to a sorting location where it may be mechanically sorted based on the classification result. Different angles assist with imaging of insects by providing cross-checks between the different views and provide a solution for insects in awkward positions that would be hard to work with using say a single camera looking from above. Tracking may be used to identify any movement of the insects on the surface, and make sure that the insects arrive at the sorting station with known coordinates that can be correlated with a classification. The tracking may be performed after detection and classification of the mosquitoes, by the cameras shown or by other dedicated cameras, and a camera calibration process may be used to sync the camera coordinates.

Reference is now made to FIG. 6, which shows a view from above of a plate 110 having two insects 112 and 114, each which a classification, M or F and coordinates. Mosquito coordinates with respect to tray coordinates are transferred between the classification cameras and camera 106 which guides the female robotic extraction arm 80.

Figure 7:
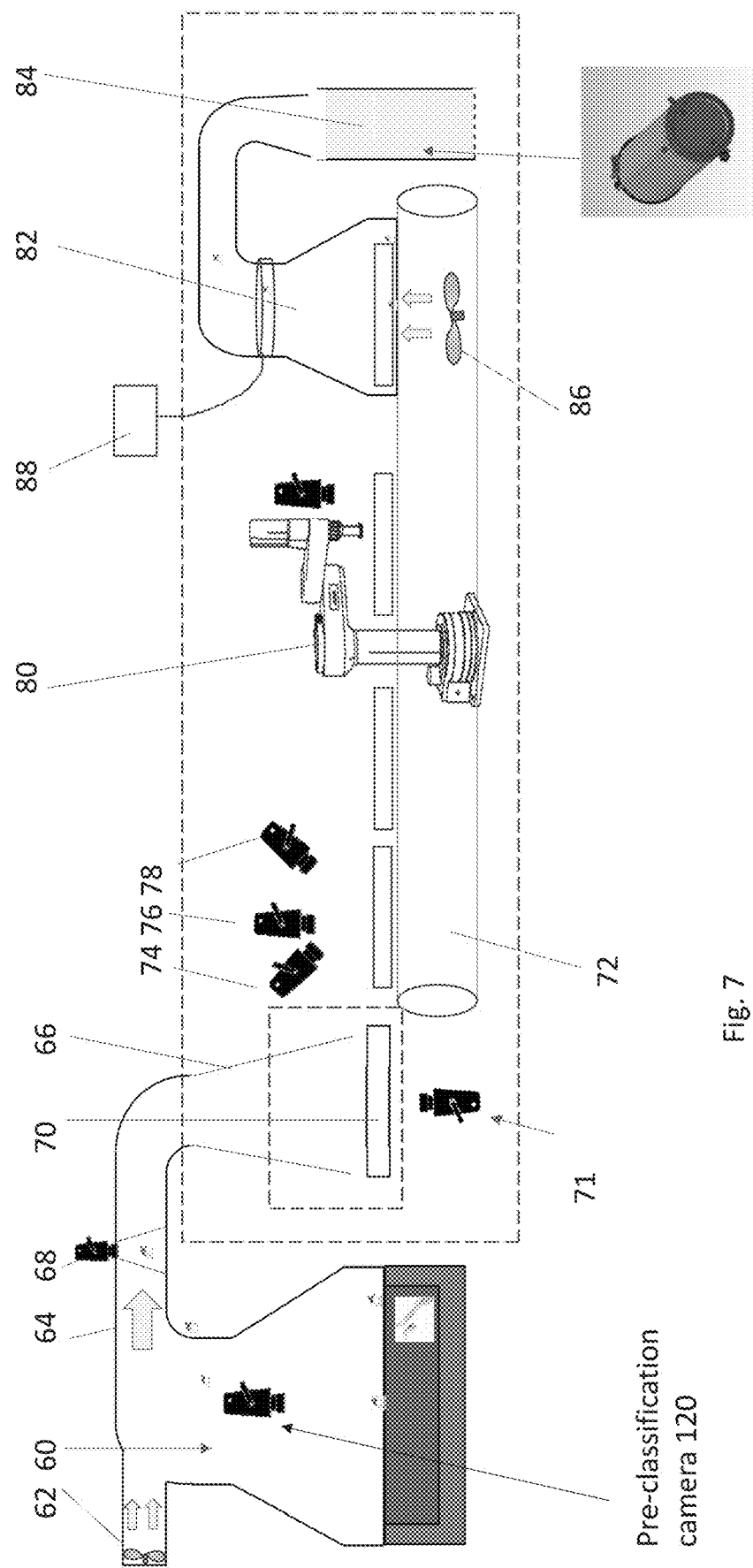
FIG. 7 is a simplified schematic illustration of another line for producing a supply of sorted mosquitoes, according to the present embodiments.

Reference is now made to FIG. 7, which is the same as FIG. 5, except that a pre-classification is carried out using a pre-classification camera 120 which has a view of the emerging insects from the insect source. Camera 71 may count the number of insects arriving. The pre-classification may allow for the removal of all unwanted insects so that no sorting is needed at the conveyor.

Reference is now made to FIG. 8, which is an embodiment in which mosquitoes are first immobilized in the immobilization area/chamber within funnel 66, and there is no need for any sorting process. In this embodiment, the assumption is that the mosquitoes are already sorted so that all those arriving in the immobilization area are of the same gender. Either there was a pre sorting process inside the rearing compartment, as per FIG. 7, or all pupas were male pupa only etc. The camera 71 at the immobilization area may count the number of mosquitoes arriving. Once a threshold is reached, a trigger is initiated and the plate, or tray or even a net like structure with square like boundaries, moves on the conveying system. A queue of trays may form and when the first tray in a queue reaches the loading station at suction arm 82, the conveyor may stop or the plate may be unloaded from the conveyor, and the loading system loads the mosquitoes say all in one go with a large diameter suction unit, but it is possible to have a smaller unit connected to an X-Y robotic arm which may be potentially guided by a camera and perform suction of mosquitoes one after the other. The mosquitoes are then loaded into a cartridge 84. Loading is performed by puffing the mosquitoes from the net, either by suction from above, or blowing air from below, or a combination. Cartridge 84 may have a door with an axis, so that feed pipe 124 is inserted into the cartridge to open the door. Upon completion of puffing, the pipe 124 is moved up, and the door then automatically closes. The cartridge is moved away, and another empty cartridge is then brought, while another tray with mosquitoes is also placed under the loading unit. The empty tray is then moved with the conveyor, and may automatically be cleaned by dispensing water from above or manually and returned for reuse to the designated immobilization station.

The image classification may involve obtaining feature extractions from the different cameras. Multiple cameras mean a multiple dimensional view of the same feature and thus may make the resulting classification more reliable.

As discussed above, classifications may be obtained separately from different cameras or from different features, and a classification rule may be used to decide between different classifications of the same insect. For example the following table provides a decision policy for two neural networks working on an insect image. It will be noted

| True status | Algorithm decisions | Probability | Decision | Accuracy (right decision) |
|---|---|---|---|---|
| F (female) | FF | $0.9^2$ | F (Female) | 0.99 |
| F | FM | $0.9*0.1$ | F | |
| F | MF | $0.1*0.9$ | F | |
| F | MM | $0.1^2$ | M (Male) | |
| M (Male) | FF | $0.2^2$ | F | |
| M | FM | $0.2*0.8$ | F | |
| M | MF | $0.8*0.2$ | F | |
| M | MM | $0.8*0.8$ | M | 0.64 |

As shown in the table, if two different neural networks, look at the same mosquito, each using a different image, then the accuracy in prediction of females is increased, if using a rule for stating an object is a female if any of the two models states it is a female.

In the example, the accuracy for actually detecting a female is 90%, actually detecting males is 80%, and falsely predicting a male is 10% while falsely predicting a female is 20%. Nevertheless removing all detected females under such a rule gives 99% accuracy, that is where the classifications are male and female, the rule of retaining any insect for which all classifications are male and removing any insect for which any classification is female, gives very accurate results.

If the rule being used is that a mosquito is stated as a female, then if any of the models decide a particular insect is a female, then the accuracy for females gets higher. A synchronization module may use two or more models, such as Neural Networks, each receiving a different image of the same mosquito and cameras may be at the same angle, but one located where the mosquitoes emerge, and another where they are knocked down on a surface, and/or cameras can be located at different angles around a surface with mosquitoes, to view the same mosquito at different angles. Each camera may perform tracking to provide updated coordinates for the next camera.

Figure 10:
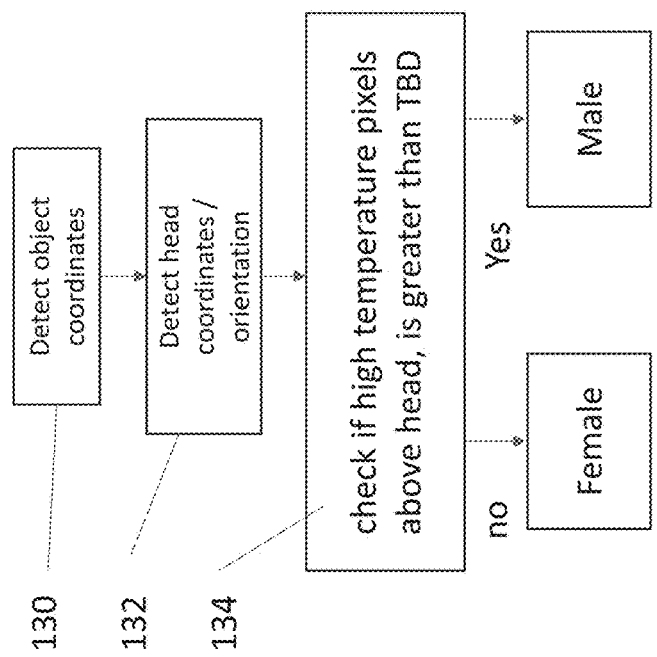
FIG. 10 is a simplified flow chart illustrating a procedure for classifying mosquitoes into male and female based on infra-red imaging, according to the present embodiments.
Figure 9B:
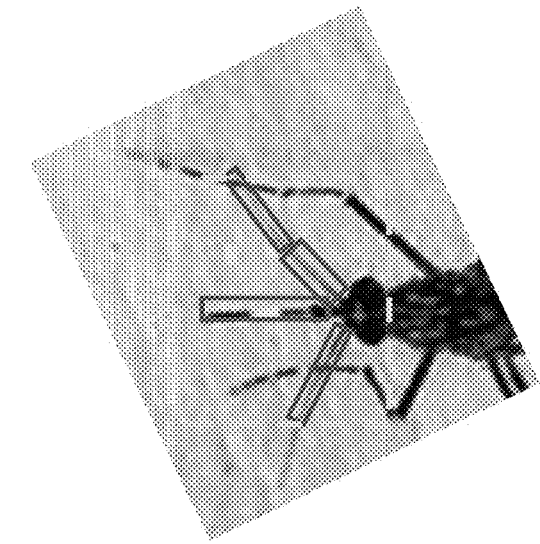
FIGS. 9A and 9B are views of male and female insect heads respectively under an infra-red camera.
Figure 9A:
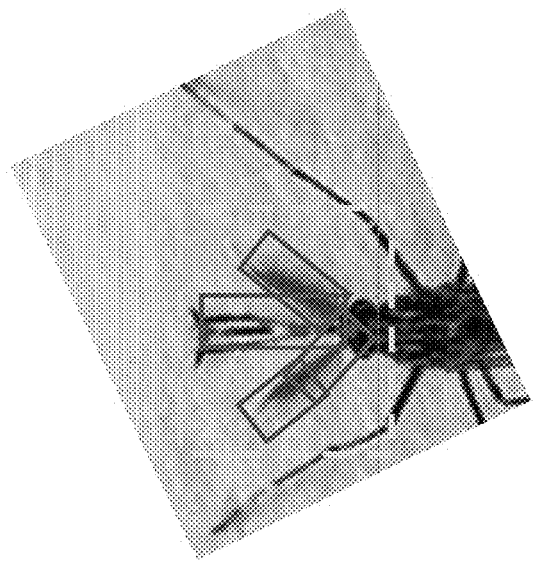

Reference is now made to FIGS. 9A, 9B and 10, which illustrate a classification method based on fusion of data from cameras where one of the cameras is an infra-red camera. FIG. 9A shows the head features of a male mosquito. FIG. 9B shows the equivalent features of a female mosquito and FIG. 10 illustrates a flow chart of a method of using the features in FIGS. 9A and 9B for classification of the insects into male and female classes.

A possible synchronization between cameras is a fusion of data from cameras having the same mosquito in their Field of View, while each camera has a different spectral lens.

For example there may be two cameras, one IR camera, and another optical.

Creating a fusion between the camera's output, increases the accuracy for success of gender prediction.

The insect may be detected by the optical camera, and then the IR camera may provide data about the temperature of the object at different areas, and the additional information increases the accuracy of prediction of the result.

Comparing FIGS. 9A and 9B, shows that the area beyond the head may yield a larger area with higher temperature for a male than for a female.

Hence, once the mosquito is detected 130 and the head is located 132, then sensing from a thermal camera may identify the temperature above the head area 134 and increase the accuracy of the male/female classification.

In embodiments, instead of an airstream, insects may be presented onto the collection area by a robot arm that places the insects on the plate etc. The insects may be placed geometrically to fill the plate in an efficient manner. The insects may be placed on a location which is stationary at the time or is already moving. If the plate is stationary then filling the plate may trigger motion.

In embodiments, suction may be provided on the opposite side of the plate, so to create pressure differences between the two sides of the plate where the mosquitoes stand, to support the flow of air through the plate. Without such suction, there may be back pressure causing turbulence.

Reference is now made to FIG. 11 which illustrates a feeding station 140. Along the conveyor 72, there may be provided a feeding station 140 which is a region which is slightly warmer than the rest of the conveyor so that insects may feed but not fly away. Sugar water, say soaked in a sheet 141, may be provided through a netting 142 in a region that is substantially free of the immobilizing agent or cooling. The conveyor in general may for example be kept at or below six degrees and the feeding area at above six degrees. The use of plates may help to transport a group of insects to such a feeding area or feeding station. The sheets soaked with sugar water can be replaced, and sugar water may spread out to any point along the conveyor with assistance.

The use of feeding stations may solve the problem of loading mosquitoes into cartridges prior to feeding them, and make sure the insects are strong enough before their release.

Figure 12:
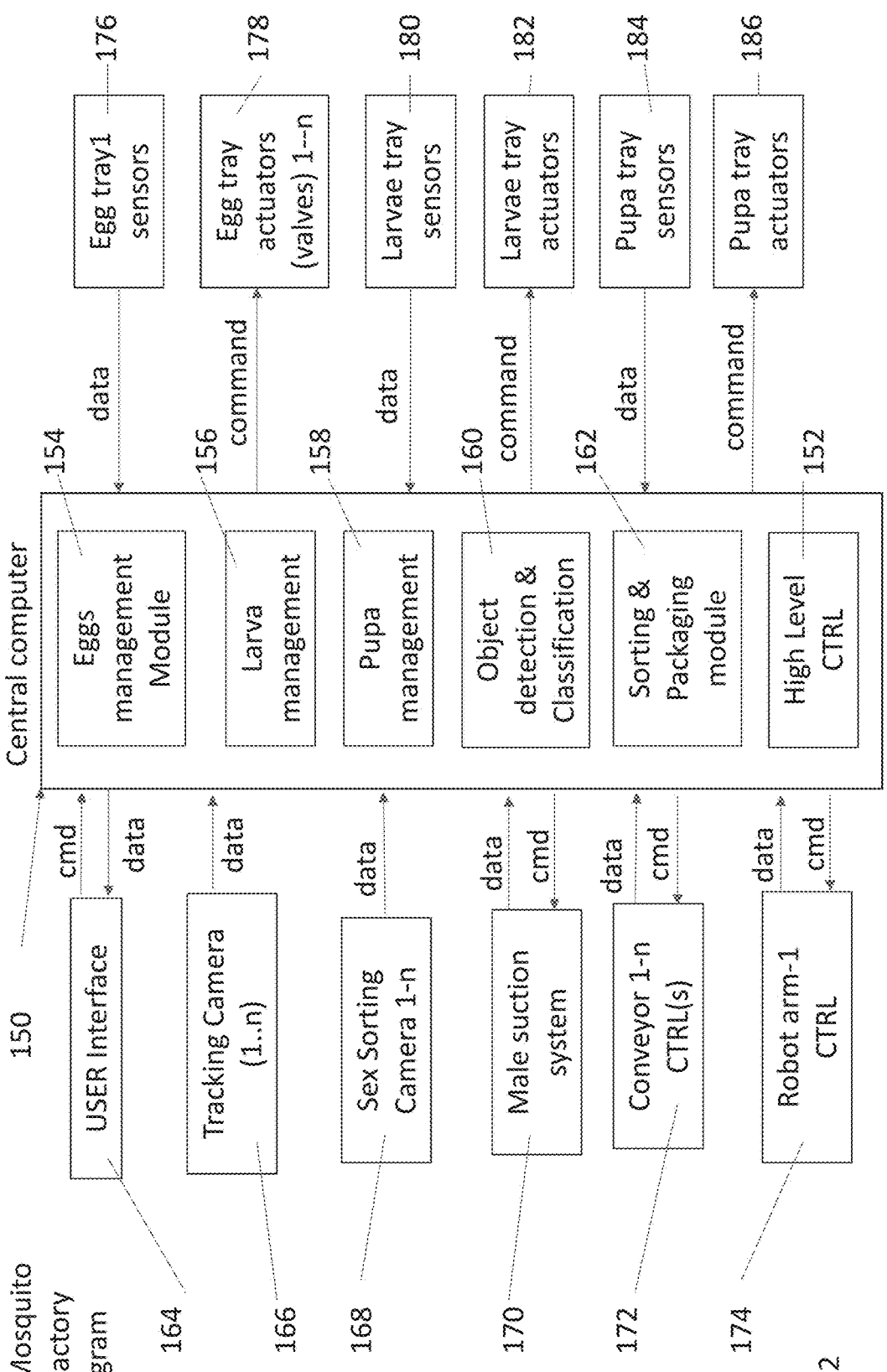
FIG. 12 is a generalized block diagram of a control system for an insect hatching and sorting factory, according to the present embodiments.

Reference is now made to FIG. 12, which is a simplified block diagram of a control system for an automated insect rearing factory according to the present embodiments. A central computer 150 has modules for high level control 152, egg and hatching management 154, larva management 156, pupa management 158, detection and classification 160 and sorting and packaging 162. The computer has input modules user interface 164, tracking cameras 166, sex sorting cameras 168, male extraction or suction system 170, conveyor controls 172 and robot arm control 174. For input/output there are also egg tray sensors 176, egg tray actuators 178, larva tray sensors 180, larva tray actuators 182, pupa tray sensors 184 and pupa tray actuators 186.

Figure 13:
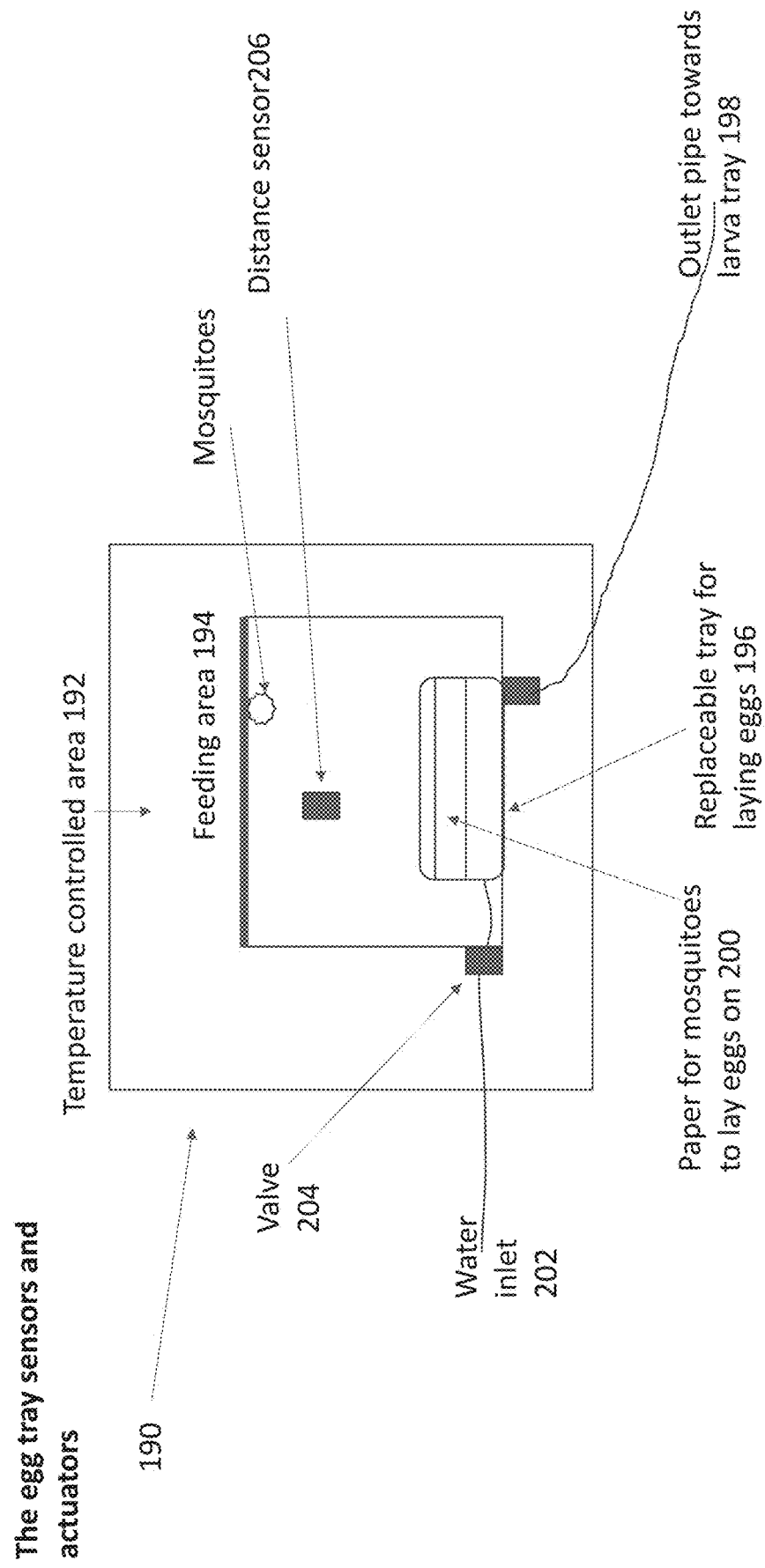
FIG. 13 is a simplified diagram showing an arrangement for obtaining eggs from mosquitoes, according to the present embodiments.

Reference is now made to FIG. 13, which illustrates an egg tray system 190. Female mosquitoes are encouraged to lay eggs in an egg tray which fills with water. Within a temperature controlled area 192 the insects are provided with a feeding area 194 and a replaceable tray 196 in which to lay their eggs. The replaceable tray may have an inner slope to ease drainage of water into an outlet pipe 198 which leads to a larva tray. Paper 200 may be provided for the mosquitoes to lay their eggs on and a water inlet 202 and associated valve 204 allows for water to be supplied to the tray. A distance sensor 206, which may be a laser or ultrasonic or other proximity sensor, detects the current water level, and the water level is gradually increased as more eggs are laid. The eggs are typically laid at the water's edge and tend to hatch following being covered by water. The tray may have a non-stick surface to prevent the mosquitoes from attaching the eggs to the tray surface.

Figure 14:
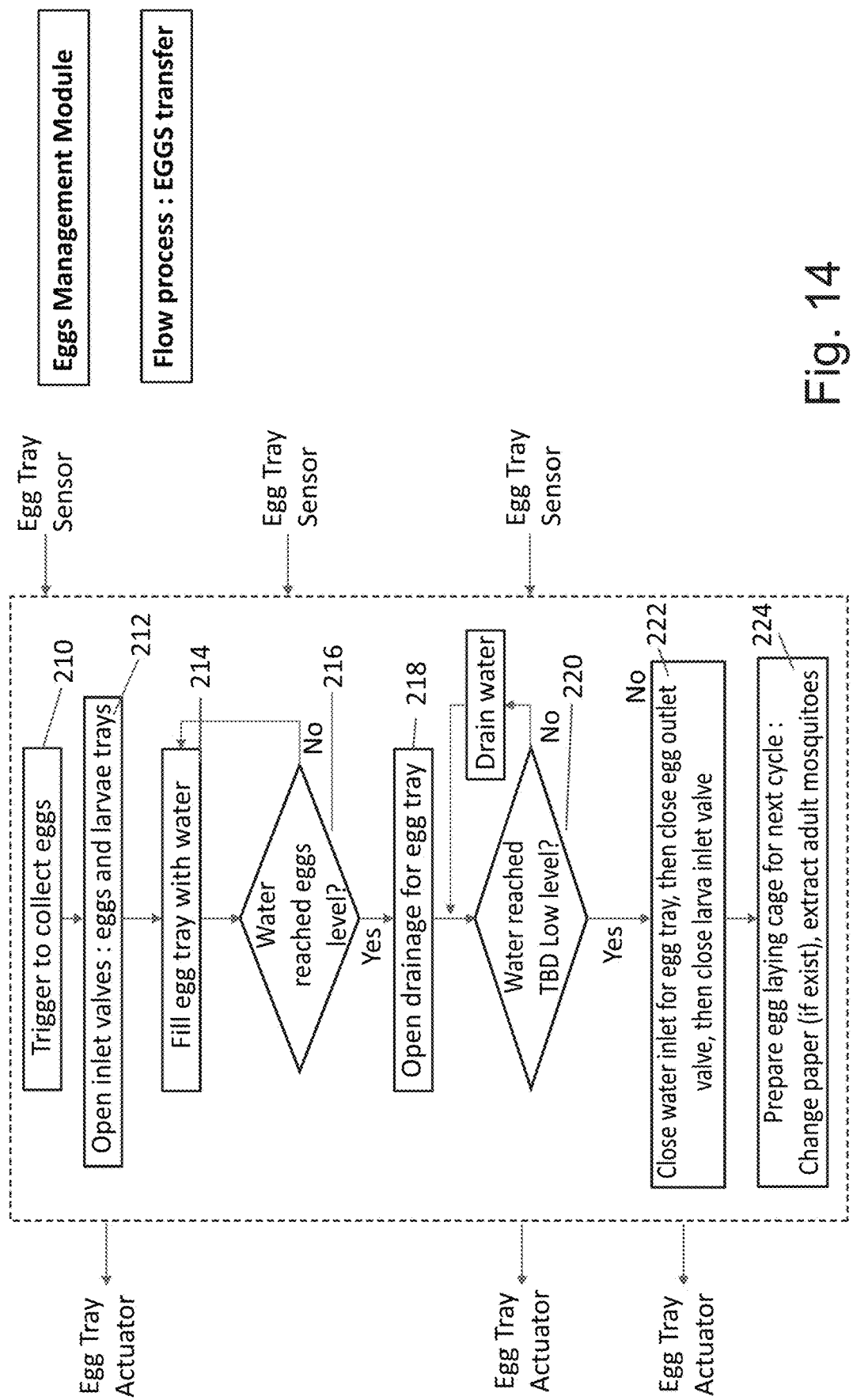
FIG. 14 is a simplified flow chart showing management of a module for managing egg laying, according to the present embodiments.

Reference is now made to FIG. 14, which is a simplified flow chart showing operation of the egg management module. The process begins with a trigger to start the egg collecting process —210. An inlet valve is opened and the trays fill with water—212. Eggs are laid and the water reaches the level of the eggs—214. The egg tray drains 216 into a larva tray which is sized to allow active swimming and feeding of insect larvae underwater, as the larvae are active, unlike the eggs and the pupae. A trigger for collecting the eggs may be based on timing since the adults entered the cage to start laying. Alternatively a camera may identify a rack of eggs at the water's edge.

A sensor may be triggered when the water reaches the level of the eggs. When the distance gets smaller as the water fills up and reaches a certain level, the controller may issue a trigger that the water has now reached the eggs.

Water is drained 218 until a preset level is reached 220, and then the inlet for the egg tray, the outlet for the egg tray and the larva tray inlet are all closed—222. Finally, in box 224 preparations are made for the next cycle. The larva tray may have upper drainage holes to deal with excess water coming from the egg trays.

Then the larva tray or egg tray is controllably drainable into a pupa tray. The pupa tray is designed for pupae to float on the surface and arranged for collection of emerging adults.

Automatic draining of water between the egg or larva tray and the receiving tray may take into account that there are different volumes of water in each tray, and thus the trays may include upper sink holes to compensate for excess water. In addition, the module may manage and control numerous trays—both sources and sinks, and then the computer may automatically open the right egg/larva tray drainage (valve), and before that automatically open the input valve for the receiving tray.

In embodiments the intermediate larva tray may be dispensed with, the egg tray draining straight into the pupa tray.

Figure 15:
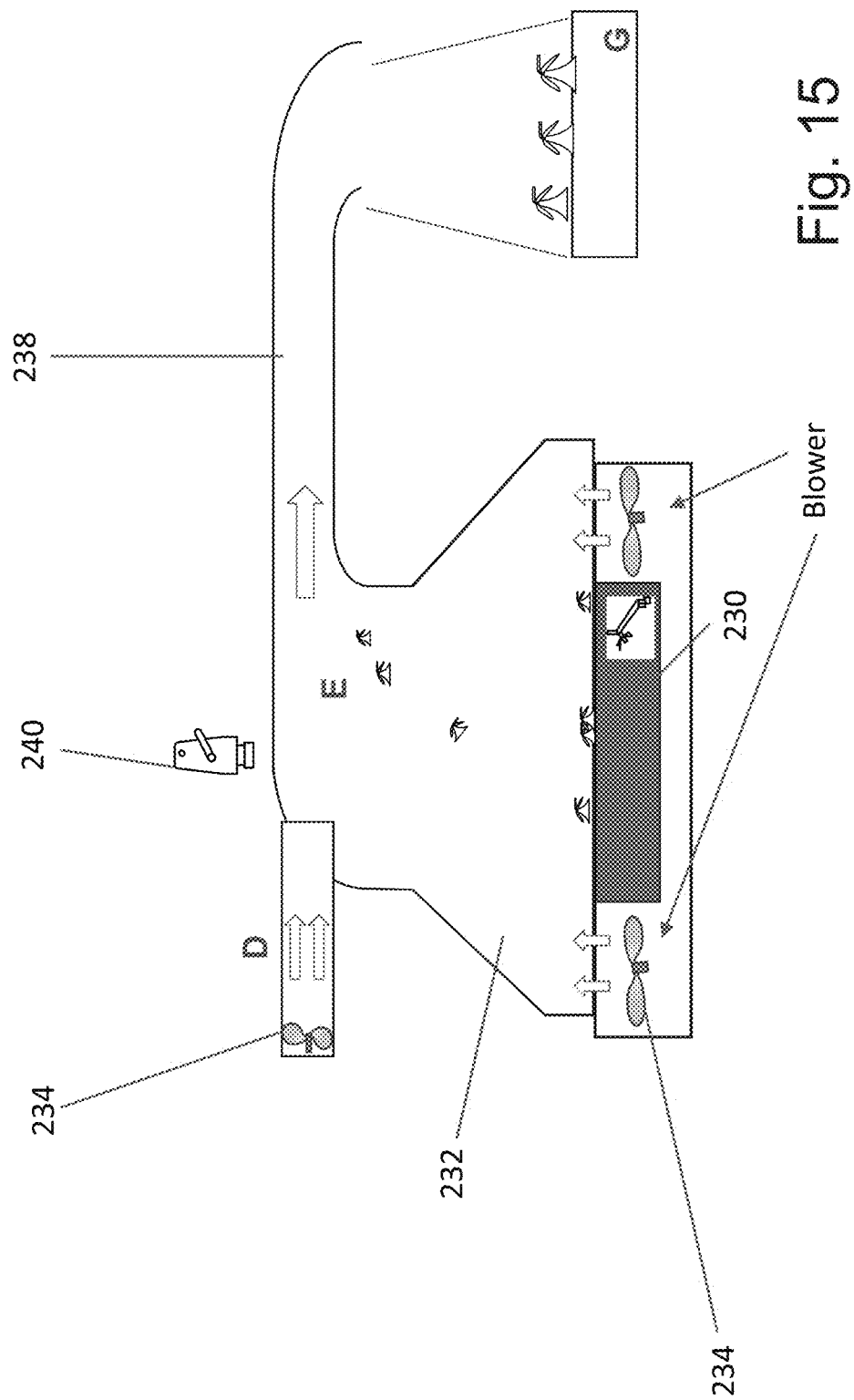
FIG. 15 illustrates apparatus for emergence of insects from a pupa tray into an airstream, according to the present embodiments.

Reference is now made to FIG. 15, which illustrates a pupa tray arranged within an insect collection system for feeding newly hatched insects to the classification and sorting system. Pupa tray 230 lies within a funnel-shaped rearing compartment 232 where blowers 234 ensure passage of air to remove insects past camera 236 into tube 238.

Guidance of the hatching insects may be carried out by blowing air from the bottom of the rearing compartment floor/surface.

The rearing compartment 232 has access to insert the pupa tray 230 either manually or automatically. Thus a tray is moved outside on another conveyor system, taken out and another tray may be inserted inside, using conveying systems that may move a small tray towards a specific position. In some embodiments, the filling of water with pupa may be performed automatically.

Cameras 240 can be located within the area where the mosquitoes are, for example inside the rearing compartment for the detection and classification step of mosquitoes during emergence, or they can be located outside, while maintaining a clear field of view by having for example transparent surface of the funnel, or above and outside the conveyor at the other section.

The advantage of locating the cameras outside as illustrated, is ease of maintenance, as well as making sure mosquitoes as they emerge, do not obscure the camera lens.

The image classification module is now considered.

The Object Detection & Classification module is generic and may be adapted for the different physical embodiments:

The architecture may use still images or video frames as an input, and may synchronize between cameras for increasing resolution.

Each camera may be hyper or multi spectral\IR\Visible camera

For some cameras there is common field of view and for others no (capture different location on the mechanical system).

Figure 16:
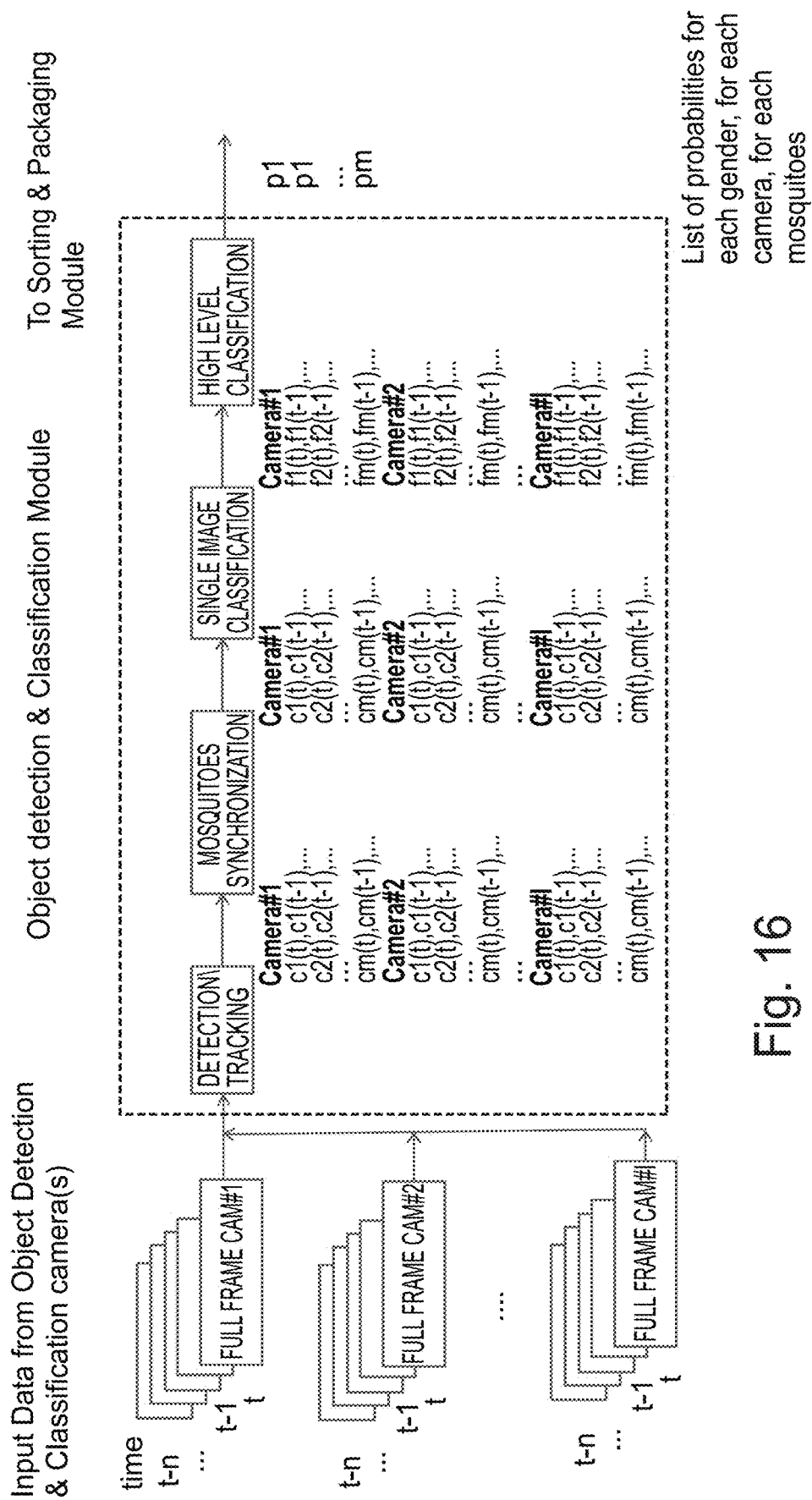
FIG. 16 illustrates operation of an object detection and classification module, according to the present embodiments.

Assuming we have: 1 cameras, n last frames and m mosquitoes detected, then the situation as shown in respect of FIG. 16 is achieved.

1) DETECTION\TRACKING: All last n full frames from each of the cameras are processed by the detection\tracking block, and a list of image crops are output: thus $c1(t)$, $c1(t-1)$, ... are last crops (small images) from each camera. In the first frame a detection algorithm will be used and later on a tracking algorithm. In case tracking fails the detection algorithm may be applied again. For objects detected in the frame, then for the next n frames and for these objects, the tracking algorithm is used.

2) MOSQUITO SYNCHRONIZATION: All of the crops are synchronized between cameras. The output of this block is again last crops from each camera but with the indices corresponding: c1 in camera # x is the same mosquito as in c1 in camera # y.

3) SINGLE IMAGE CLASSIFICATION: Each of the crops is being classified (male\female). This block outputs the prediction or additional features used for prediction: $f1(t)$, $f1(t-1)$, ... for each crop.

This generic architecture enable the algorithm to finish at this point and provide the gender prediction, or move to the next step:

4) HIGH LEVEL CLASSIFICATION: A high level classifier employs all information of each mosquito (from previous n frames) and yield a final decision (male\female):p1, p2, ..., pm.

The frame history may be used to give a time dimension to the information. For example high level information about insect emergence may be obtained from a sequence of frames over time of the same insect during the several minutes of the emergence process.

Reference is now made to the Mosquito synchronization block, which works based on the following methods:
Camera calibration (in case where cameras share same field of view)
Order of appearance, for example where different locations on the mechanical system preserves order of arrival.—A controller may receive notification from a first camera regarding the mosquito gender and when it flies away, something possibly detected by another camera at a different location. Then a further camera sees the mosquito arriving within its field of view. Based on the delay between the two events it is possible to synchronize between the mosquitoes at the two cameras.

Siamese network may verify that two mosquitoes from different non overlapping cameras are the same Implementations of the various blocks may use algorithms according to the following table:

| Block | Possible Algorithms |
| --- | --- |
| Detection\Tracking | Detection: YOLO(You only look once*), Faster RCNN(*), Viola Jones, subsequent frames differences Tracking: Kalman filter, Contour tracking, Particle filter |
| Single image Classification | Classic algorithms: HOG (histogram of oriented gradients) + SVM (support vector machine) LBP (local binary pattern) + Decision trees Deep CNN: Inception v4 Xception Capsulenet Siamese Network (**) |
| High level classification | RNN (Recurrent neural network), LSTM(Long short-term memory), GRU(Gated recurrent unit), Attention model |

Figure 17:
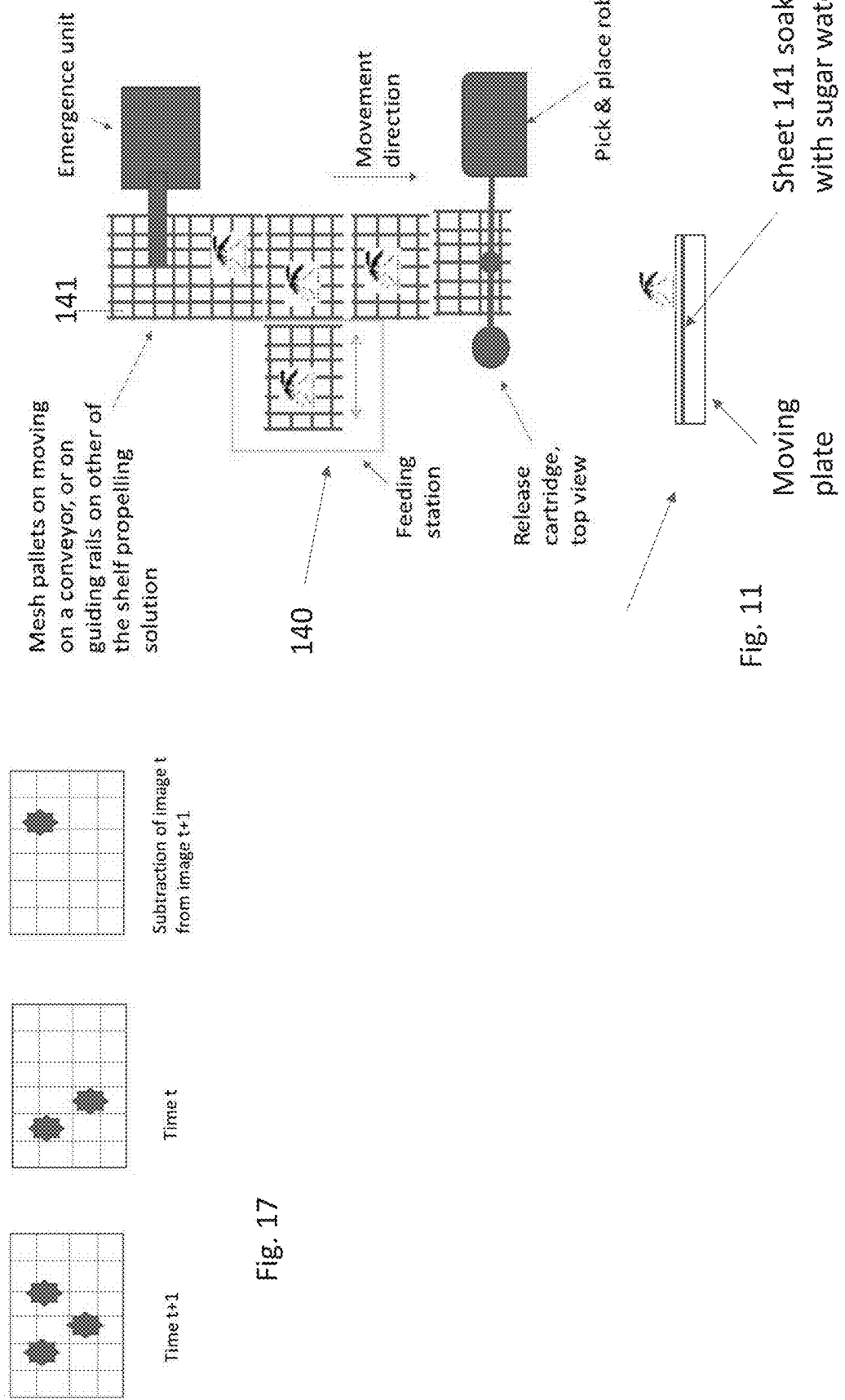
FIG. 17 illustrates using successive frames to indicate presence or absence of insects, according to the present embodiments.

Reference is now made to FIG. 17, which illustrates identifying the arrival of a new insect in a new frame. FIG. 17 shows a sequence of two frames with a constant background and from time to time a new object (a mosquito) appears on the background. A third frame is generated by subtracting the new frame from the old frame.

Detection is easier than the classic problem of object detection in an image, and may be based on a morphology operation on the image differences.

Possible steps may include:

Denote diff to be the binary image of different between two adjacent frames.

Let diff_open be the image after applying morphology opening on diff

Store locations of n highest connected components of diff_open

If these locations are consistent for at least m more frames consider it as a new mosquito.

Regarding classification, it is possible to search, not for an insect as a whole but specifically for the head area with the antenna of the mosquito as this is the part that is different between the male and female.

Figure 18:
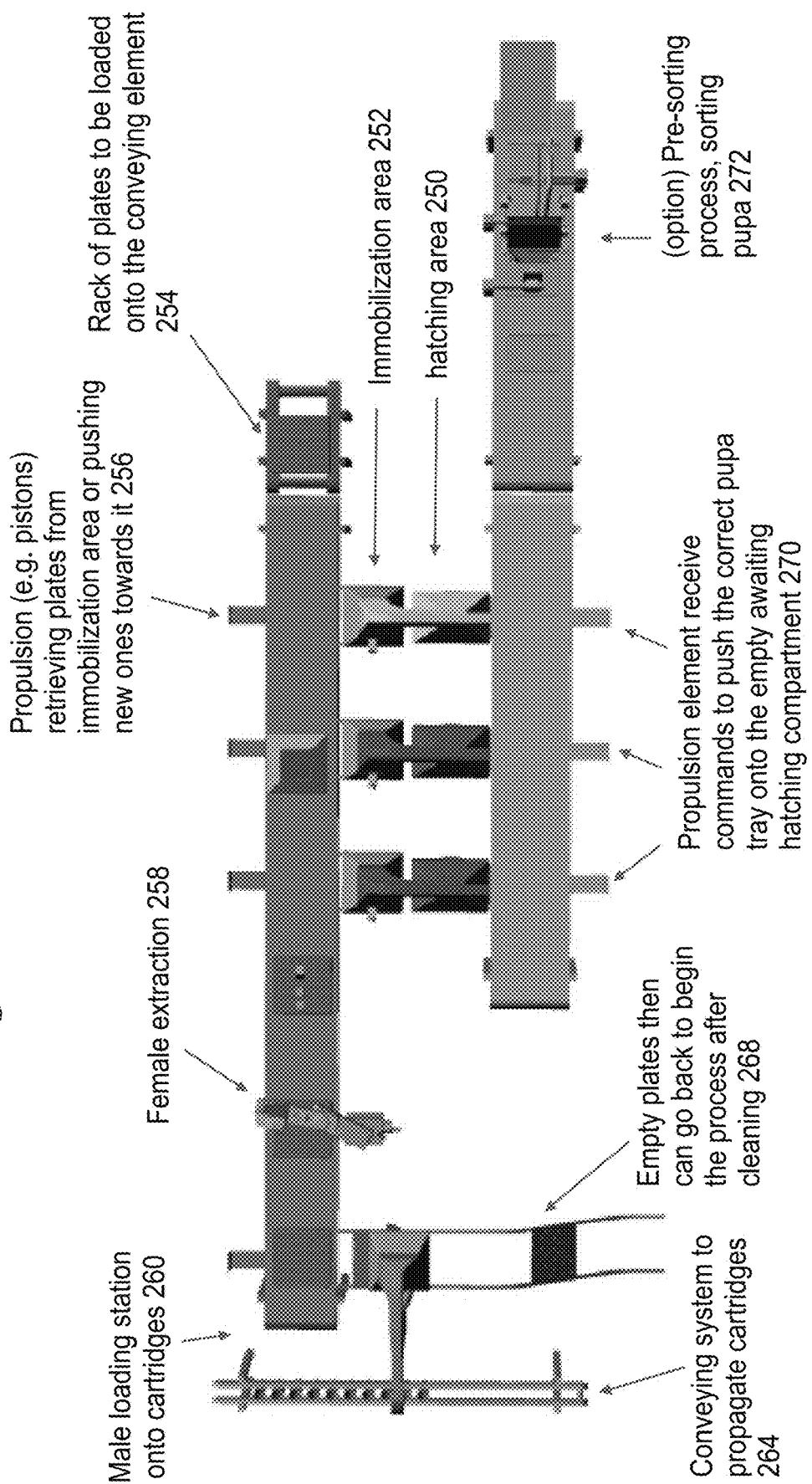

Reference is now made to FIG. 18, which is a schematic diagram of a sorting and packaging apparatus, for simplicity not showing the cooling apparatus. Hatching areas 250 lead to immobilization areas 252 where plates are received from racks 254 using propulsion 256 and move from the immobilization area to the female extraction area 258 and then to the male extraction area 260. A separate conveying system 264 moves the empty and full cartridges and a yet further system takes the empty plates 268 back to the beginning. A fourth conveying system 270 manages the pupa trays, including pre-sorting 272.

Figure 19:
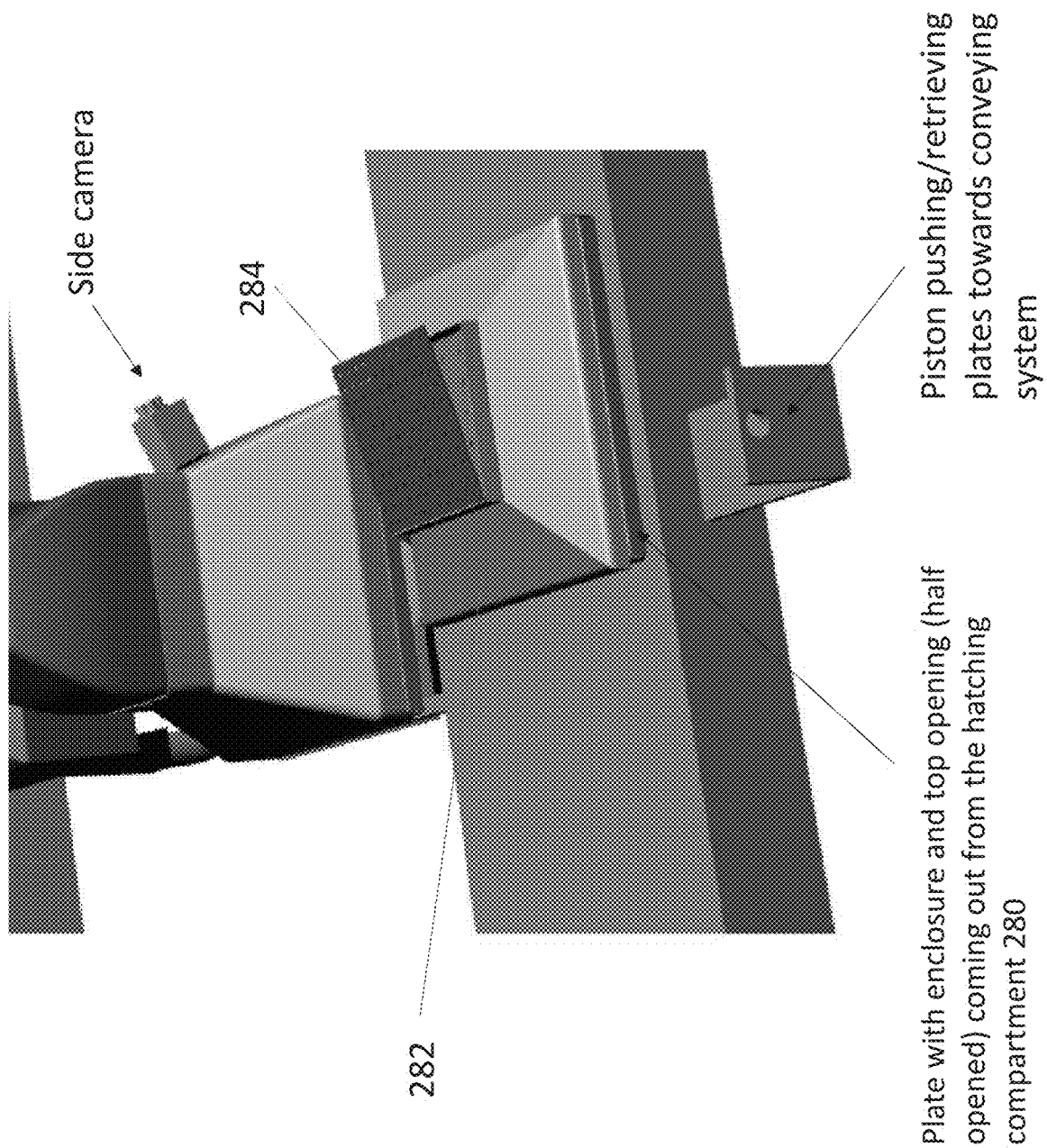

Reference is now made to FIG. 19, which shows a plate 280 with an enclosure 282 and top opening 284. It is possible to have the entire (or part) plate on which the mosquitoes land, covered by a cover with a closure that is opened when mosquitoes land on the surface, and closed later, for example when it is moved away from that position, or when an actuator closes the closure upon command.

An advantage is that instead of manipulating and conveying open plates with live mosquitoes in between stations, it is possible to convey plates with enclosures, and when needed, for example at the robotic sorting station, the enclosure may be open and females may be extracted. In that way large numbers of plates can be transferred for example over a non-cooled area, and then brought again to the robotic sorting and packaging when required.

The plate 280 is in this embodiment a surface for standing mosquitoes with a net on the bottom, and an enclosure 282 with an opening that may be automatically opened or closed in between stations.

Figure 20:
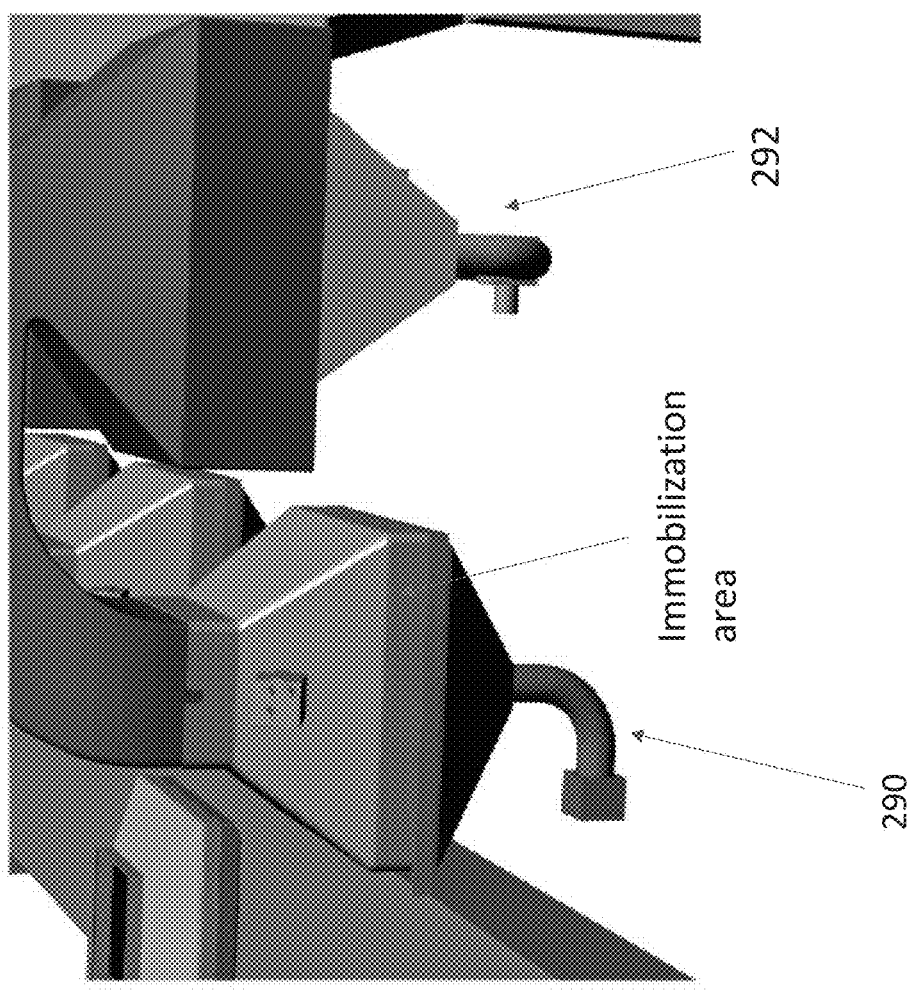

FIG. 20 shows the system of FIG. 18 from a lower perspective. Pipe 290 may provide for suction of air under the plates to create pressure differences to ensure flow of air through the immobilization chamber preventing turbulence. Air inlet 292 may provide a source for puffing the insects.

Figure 21:
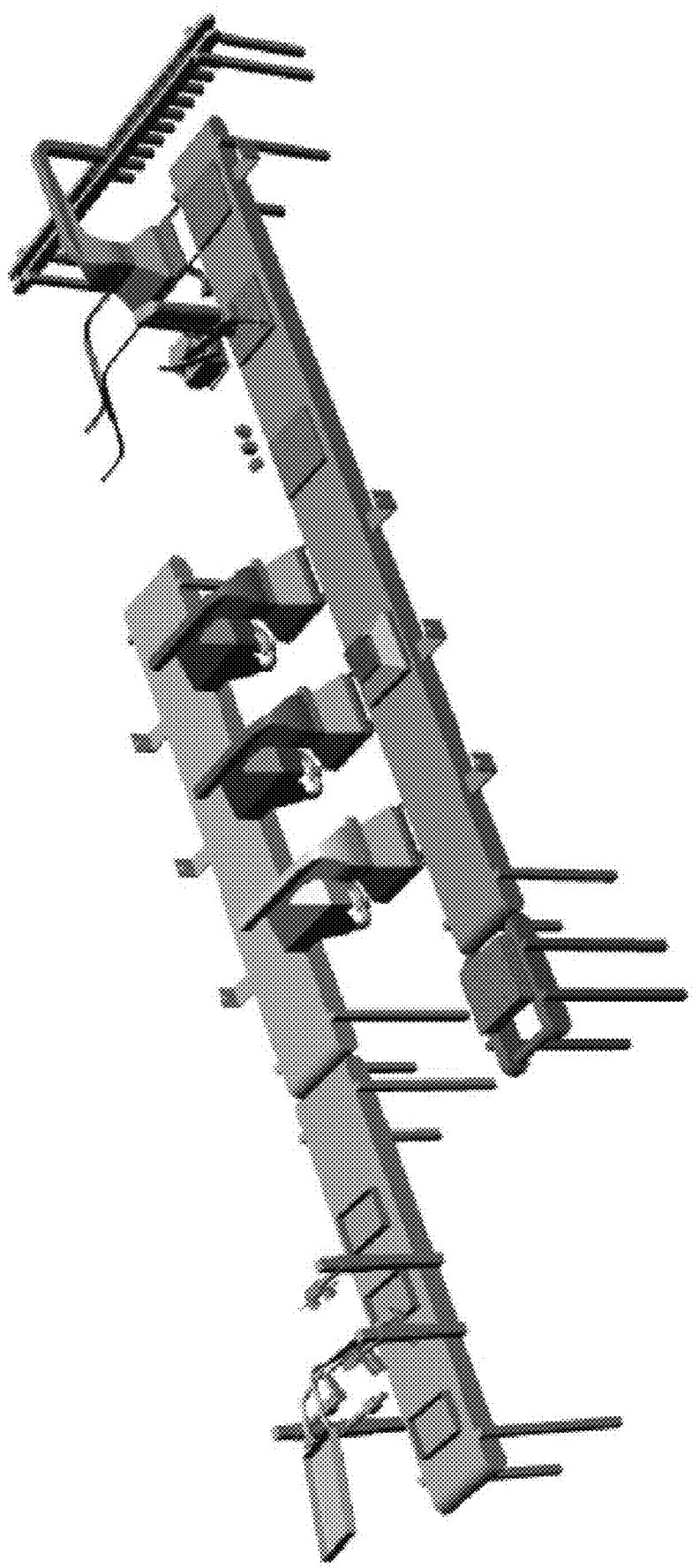

FIG. 21 is an above-side perspective view of the same system. An 8 meter long system, over 2 meter wide, may have a sorting and packaging capacity for 150,000 mosquitoes per day.

Figure 22A:
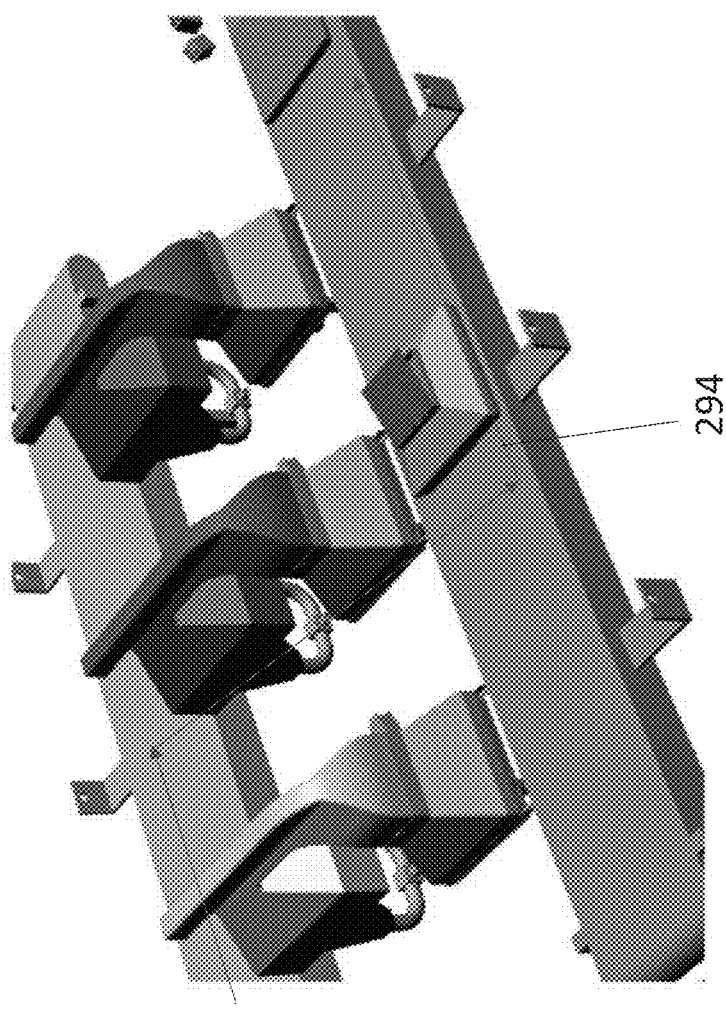
Figure 22B:
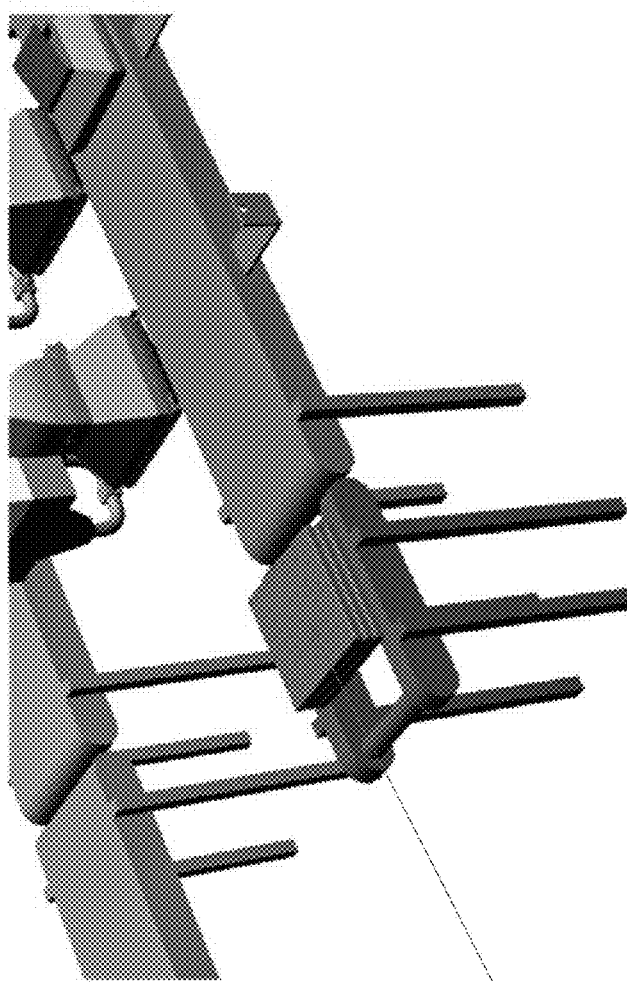

FIGS. 22A and 22B are a view from above showing arrow 294. Arrow 294 represents the general flow process direction—a tray of pupa arrives and is controllably moved towards the awaiting empty hatching compartment. The computer manages which hatching compartment is empty and needs refilling and which is still in progress with mosquitoes hatching, and landing on the net plate in the immobilization area. Once the net is full it is moved away to the next conveying system towards further stations.

Figure 23:
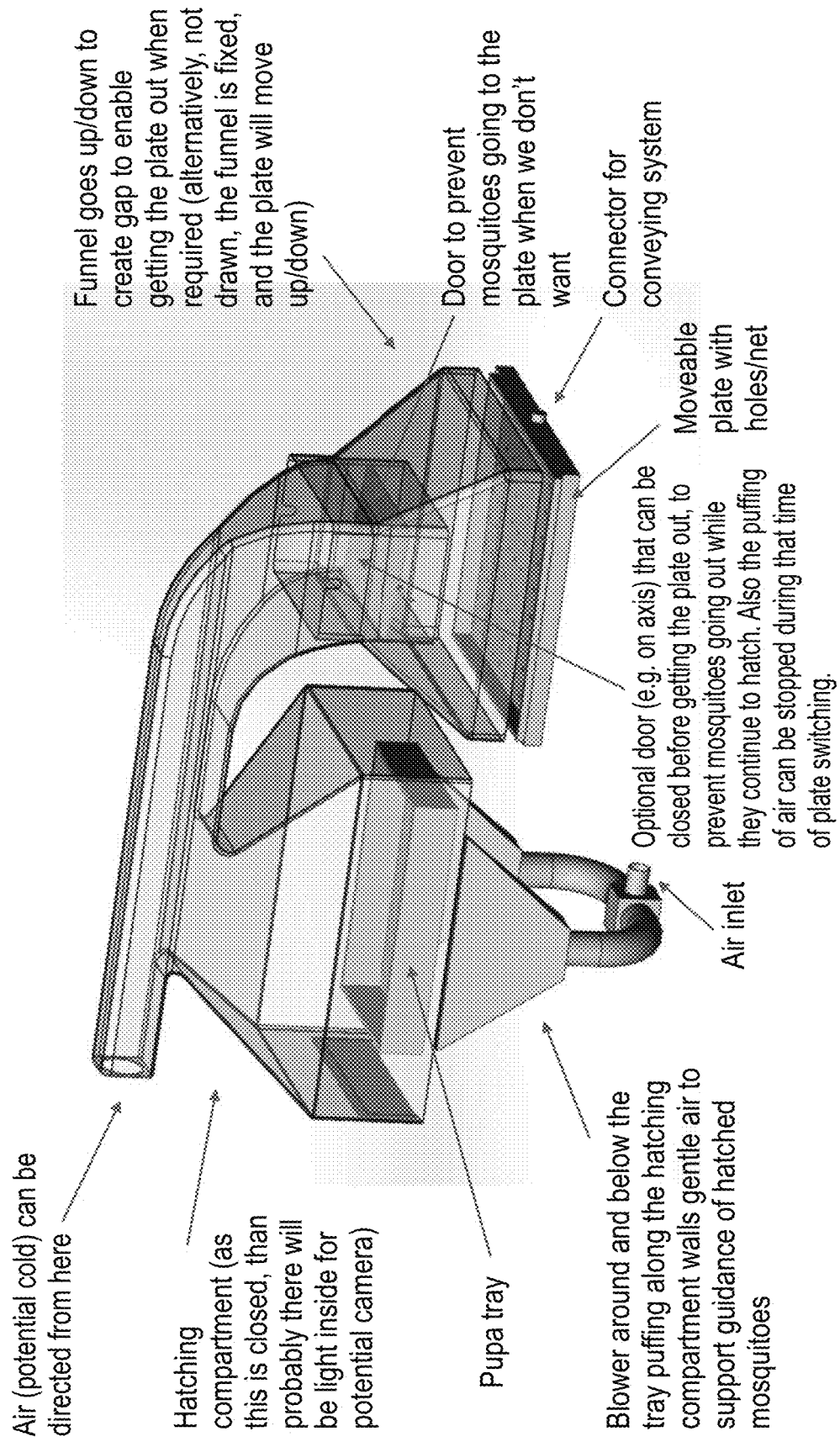

FIG. 23 is a diagram of the hatching compartment and funnel area.

Figure 24:
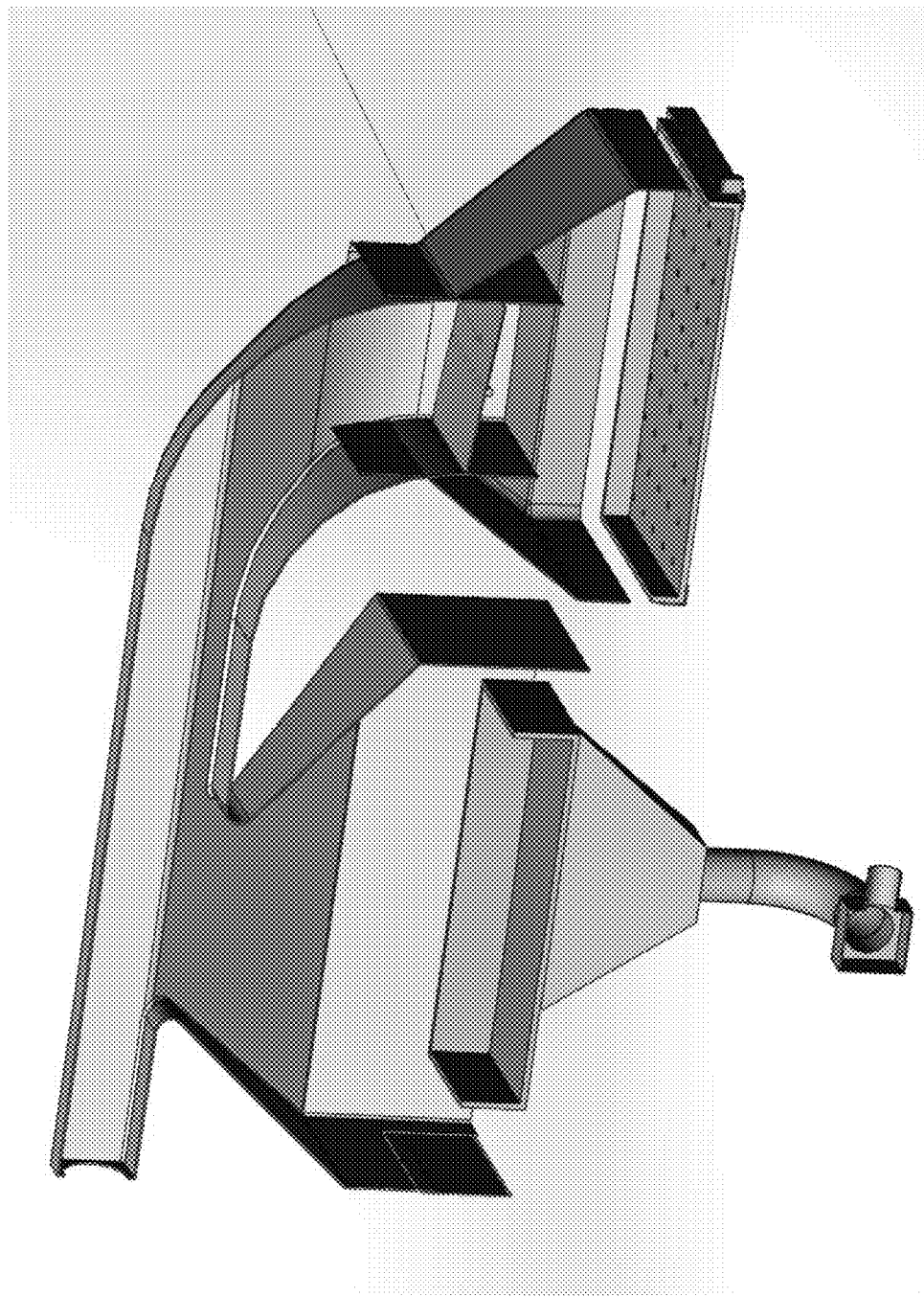

FIG. 24 is a cross section of the hatching compartment and funnel area of FIG. 23.

Figure 25:
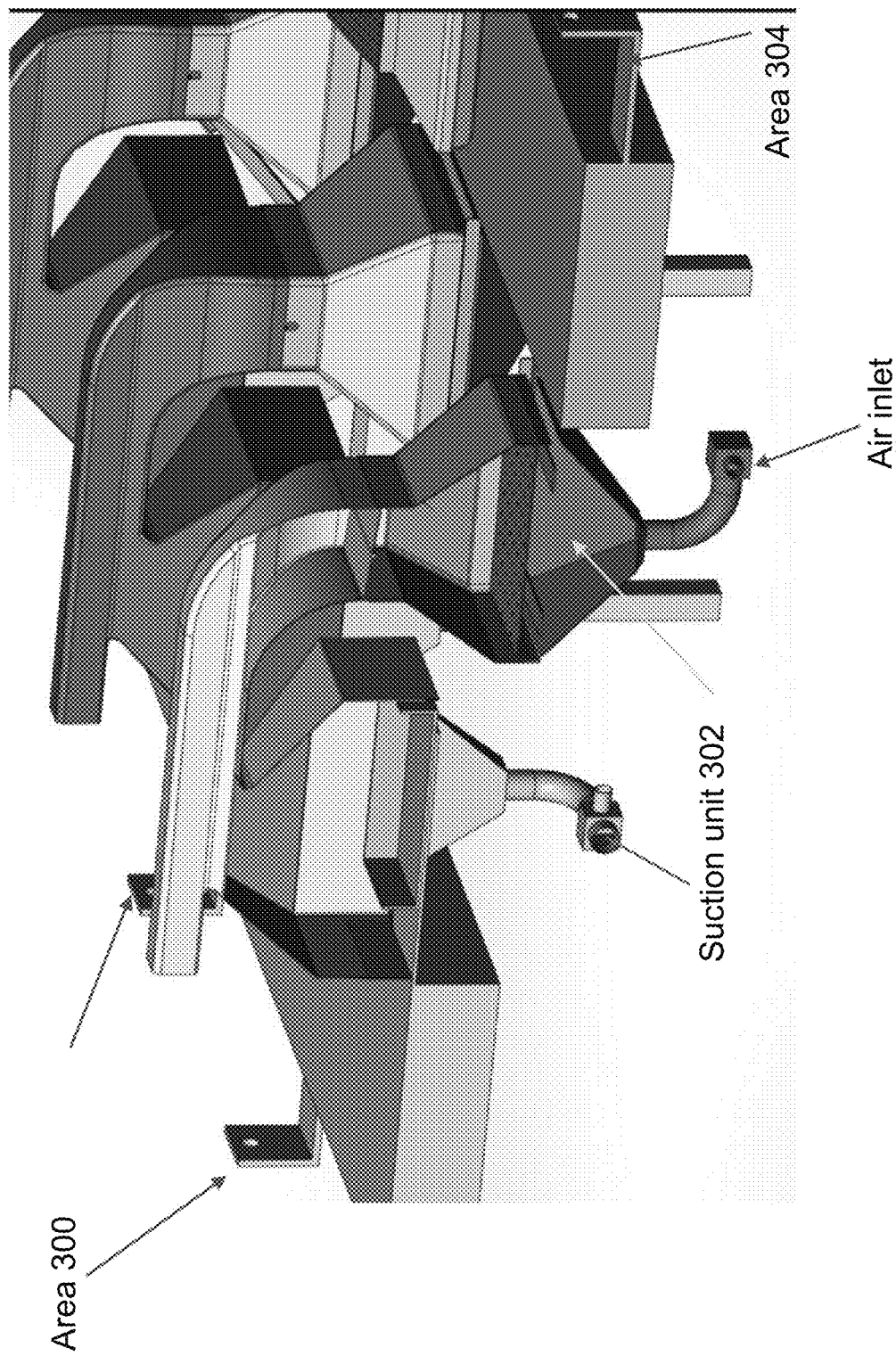

FIG. 25 is a detail of the pupa tray management. Area 300 has a mechanism, for example based on pistons, which move the pupa trays perpendicularly from a conveyor at 90 degrees towards the emergence compartments. A suction unit 302 is located below the plate area, in order to gently suck air, and help create a pressure difference between above and below the net area, in order to ensure the air is flowing downwards through the net, without (or minimizing) turbulences on the net surface where the mosquitoes land. Area 304 has a mechanism, again for example based on pistons, which move the adult mosquito tray perpendicularly from below the funnel towards the conveying system for further treatment.

Figure 26:
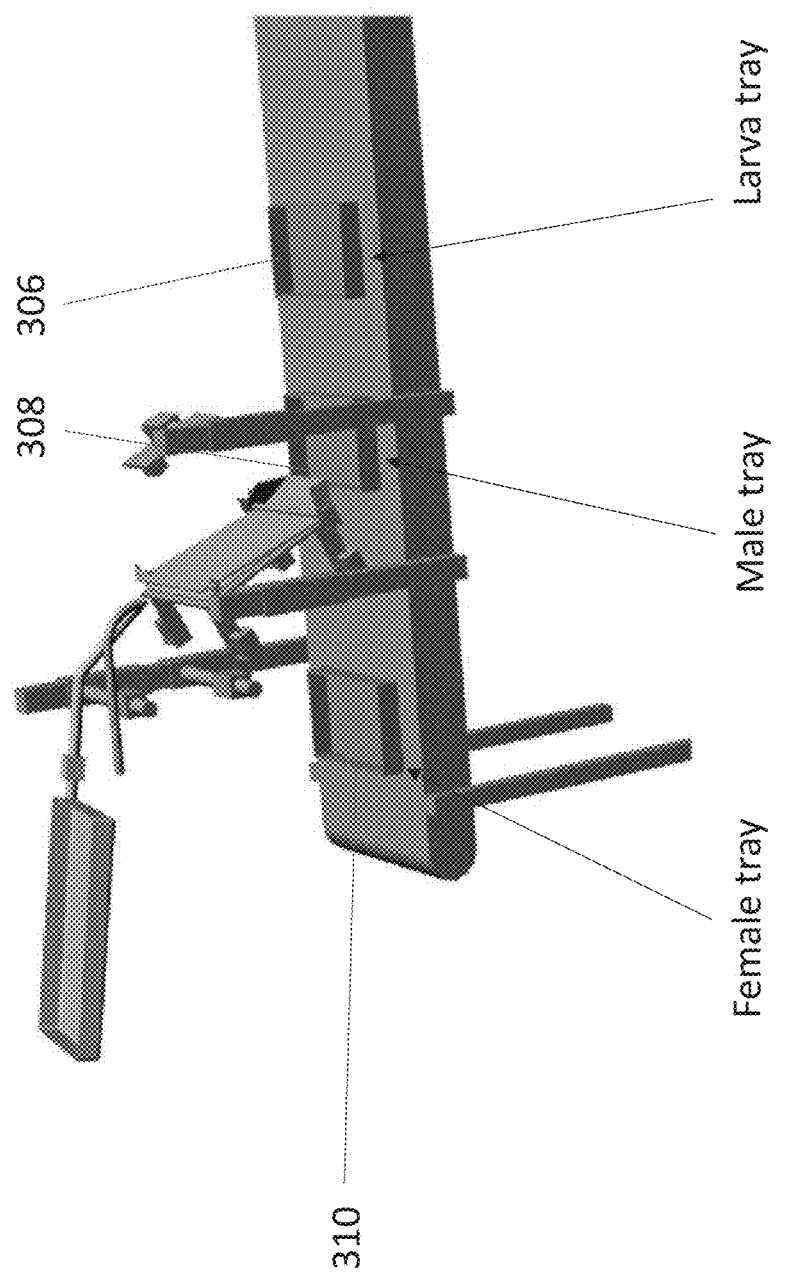

Reference is now made to FIG. 26, which illustrates larva trays in which mosquitoes grow as larva. When most are already pupa, they are transferred towards the automatic pre-sorting unit. Alternatively, they may be automatically delivered to separate pupa trays, and from there to the hatching compartments, say without pre-sorting.

Pupa are poured from the larva tray 306 into the pupa trays 308 and 310. First surplus water may spill down, either to a dedicated tray or directly to sink, and then the system may propagate the larva from the larva tray to collect the larva automatically, after which the conveying system may move and bring the male tray 308 to collect male pupas, and then potentially again it will move to collect the female pupa in female tray 310.

Figure 27:
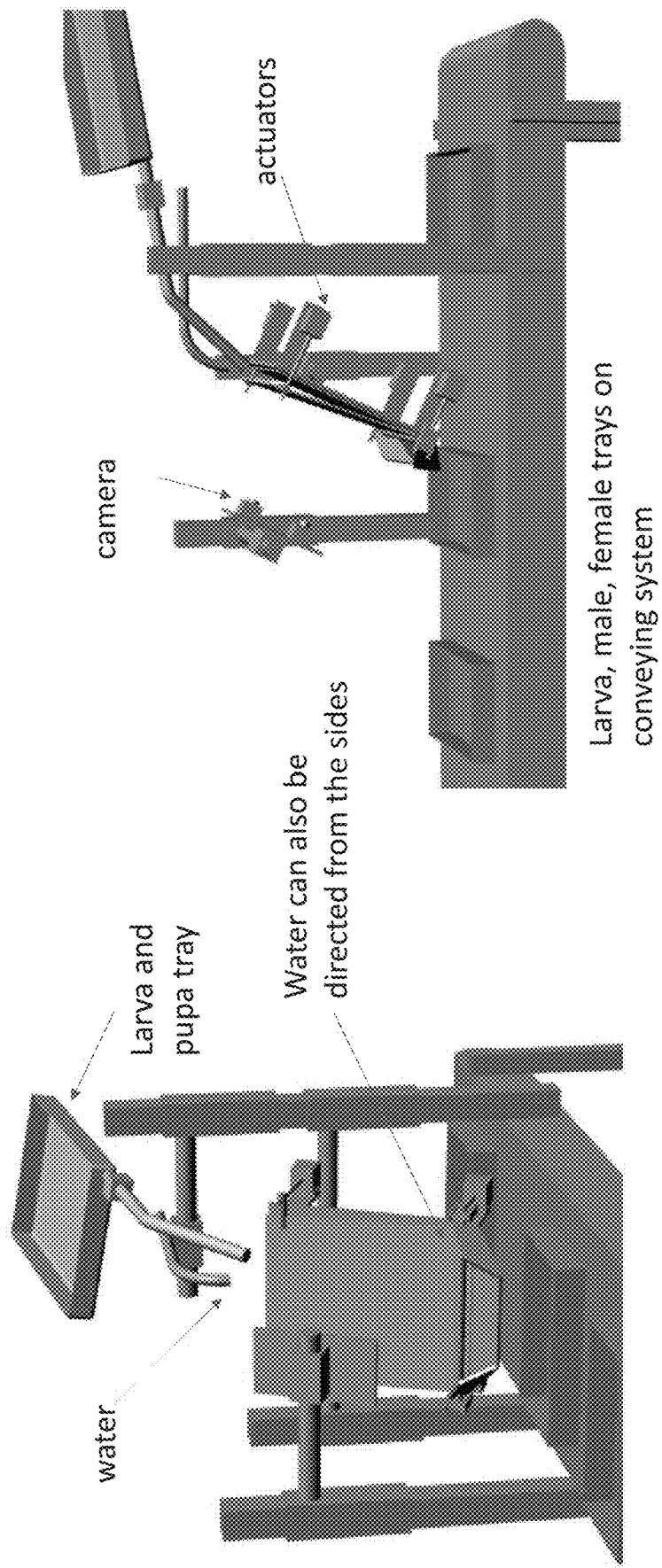
Figure 28:
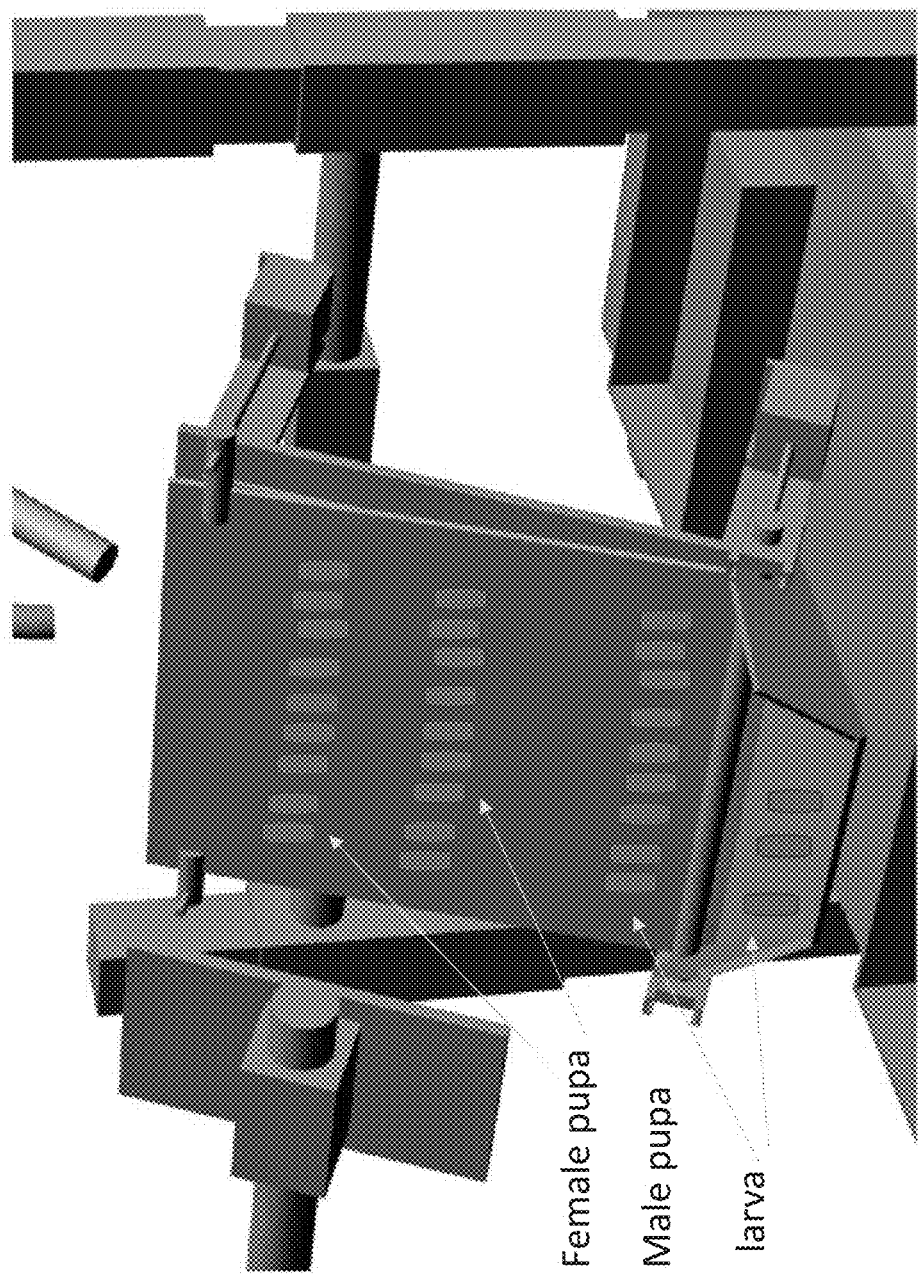

FIGS. 27 and 28 illustrate pouring of water with larva or pupa from an upper tray to lower trays on a conveying system. It is noted that the water may be poured as opposed to being sucked.

Image processing may be used to automatically manipulate the actuators to let three lines of pupa/larva go down slowly while keeping a distance between each row, and when each row arrives at the bottom it is poured into the next awaiting tray. Once done, more pupa is poured from above.

A number of ways may be used to achieve the result. In one embodiment, an image based metric may represent the amount of separation between the male pupas and the females pupas.

One option involves detecting two lines in the image using a hough transform, which takes an image as input and returns the line.

A second option is to detect two clusters (of black objects) based on k-means—and output the cluster location.

With such a metric on hand, maximization is now required.

Maximization may be achieved by training a neural network that gets as an input the current metric and returns commands to the affect the water flow.

An alternative is to use a constant pattern that alternately opens the lower and the upper spaces and uses the line locations and spacing to increase\decrease the time each space between the glasses is opened\closed.

Figure 29:
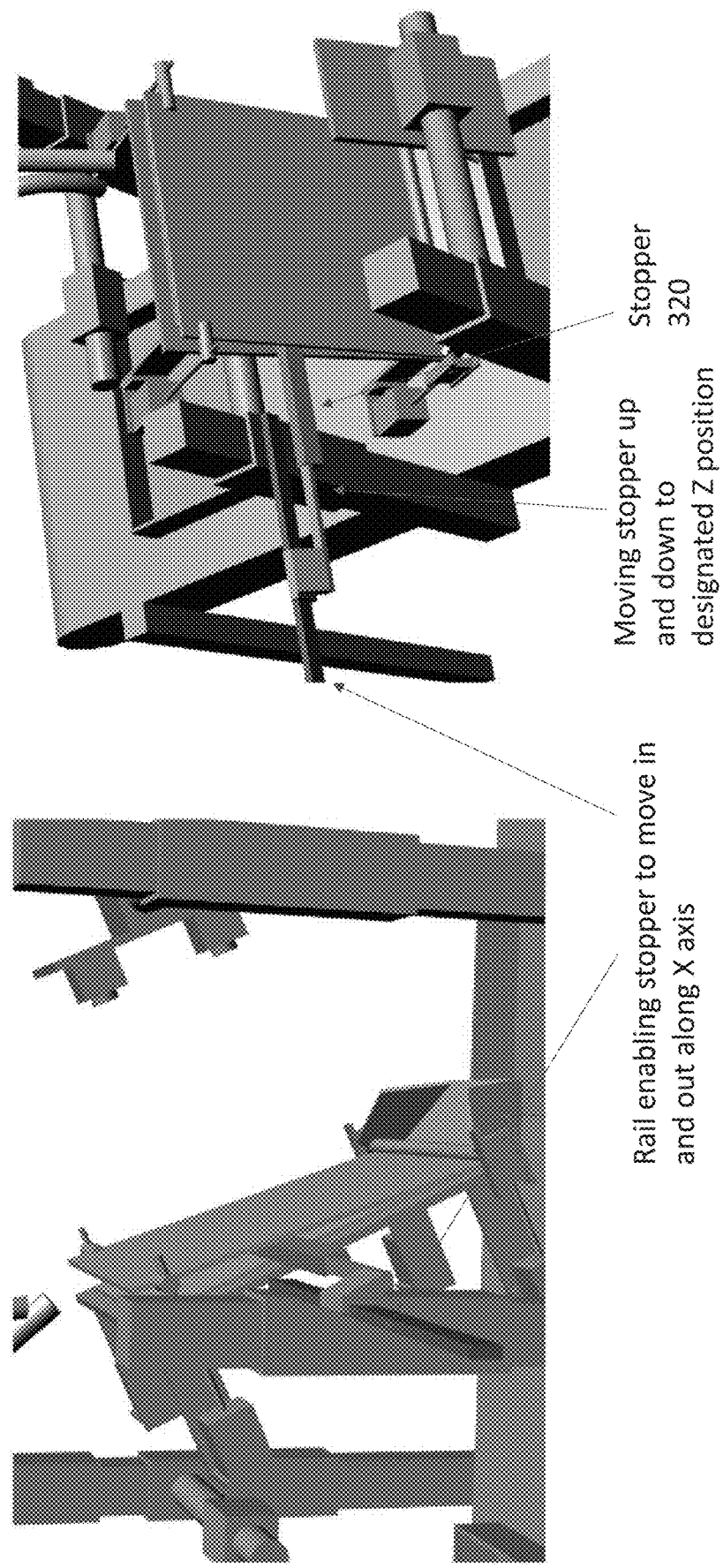

Reference is now made to FIG. 29, which illustrates an embodiment in which a moveable stopper 320 is used to increase productivity and ease automation. Again, image processing may be used to identify an upper line of pupae, which is the female line. The line is identified as described in respect of FIGS. 27 and 28. In the case of using the k-mean for detecting the clusters, then stopper 320 may be inserted between the heights of the two clusters. Once the line is detected, pouring water may stop, and a command is sent to bring the stopper 320 to the correct height, which is just below the line height, and be inserted, as shown.

The stopper provides a method of pre-sorting based on differential size between male and female pupae. The stopper is mechanical and moves in an X-Z axis.

Referring also to the flow chart in FIG. 30, once the rows are created for the first time, then the height of the upper row (female) may be detected. Then, the slope Z height is set to be a few mm (or cm) below the upper row. The stopper is inserted along the X axis, and then water is poured from the side, only above the upper row, causing all the female pupae to be flushed out, while the stopper prevents the water from reaching down to the males. Then if needed (if for example there is a larva row as well) then another stopper may be placed just below the middle row, and similarly the males are flushed to the side where they can be collected. The collected males may then be poured onto or be used as the pupa container moving on the conveyor for the next station.

In another embodiment (not drawn), a sorting plate may be rotated on its axis, for example 90 degree or 180 degree to support the flushing out of the female pupas and then males and if required larva.

There may be two stoppers on the same Z axis with two rails. One may match the width to stop the females being collected when water is poured from above, separating between the female line and the male line, and the other, for identifying the middle, male, line may be inserted just below, with a width that can stop the males mixing with larva.

In another embodiment (not drawn) instead of using two different stoppers, one stopper that can adjust its width may be used, for example with a construction similar to that of a flexible balloon like stent element. The size may be adjusted to stop the females or stop the males as desired.

Pre-sorting means that the mass of insects further down the process is some 90% male, so that further sorting can lead to much higher purity, with an aim of 1:250,000.

FIG. 31 illustrates pupa management. Full pupa trays arrive 340 at emergence compartment 342 where insects emerge and are funneled to plates 346 for sorting and packaging etc. The used pupa trays are taken away for reuse 344 as new trays. Multiple trays may be provided along a single path, but if all are emerging at the same time then they may need to be in the emergence unit at the same time. FIG. 32 shows an embodiment with multiple emergence units so that multiple pupa trays that are hatching at the same time can be accommodated.

FIG. 33 is a detail of the suction arm 82 for picking up male mosquitos from the trays and placing them in cartridges. A combination of moving plates on a rail, as opposed to a regular conveyor, and sucking the insects into the cartridges using a suction device (e.g venturi) rather than dropping them is used. Optionally, a blower from below may support the puffing of the mosquitoes towards the cartridges. The cartridges may be kept open if under cooling and be closed later, or they can be automatically closed as discussed above.

FIG. 34 is a detail of the plates 70, showing a net 350 or like element with holes on a supporting element 352. The design enables quick replacement of the plate parts for cleaning etc.

Reference is now made to FIGS. 35 to 39, which illustrate an embodiment in which each plate or net is provided above the emerging area. Again a continuous flow of insects is provided.

The mosquitoes emerge into a funnel with gentle upward suction (e.g. 0.5-1 m/sec) in order to support the flow of mosquitoes towards the net.

It is preferred to have the net as close as possible to the hatching tray, but it can also be located higher.

A sensor (e.g. camera) located above, may trigger the event for the transfer of the net or plate towards an immobilization area. In this embodiment, the immobilization area does not have to be a closed area, but simply an area where cold air is being puffed onto the net or plate holding the mosquitoes.

The plate is then transferred to a conveying system, and is moved for further treatment—such as female and or male classification and extraction as with the other embodiments.

Figure 35:
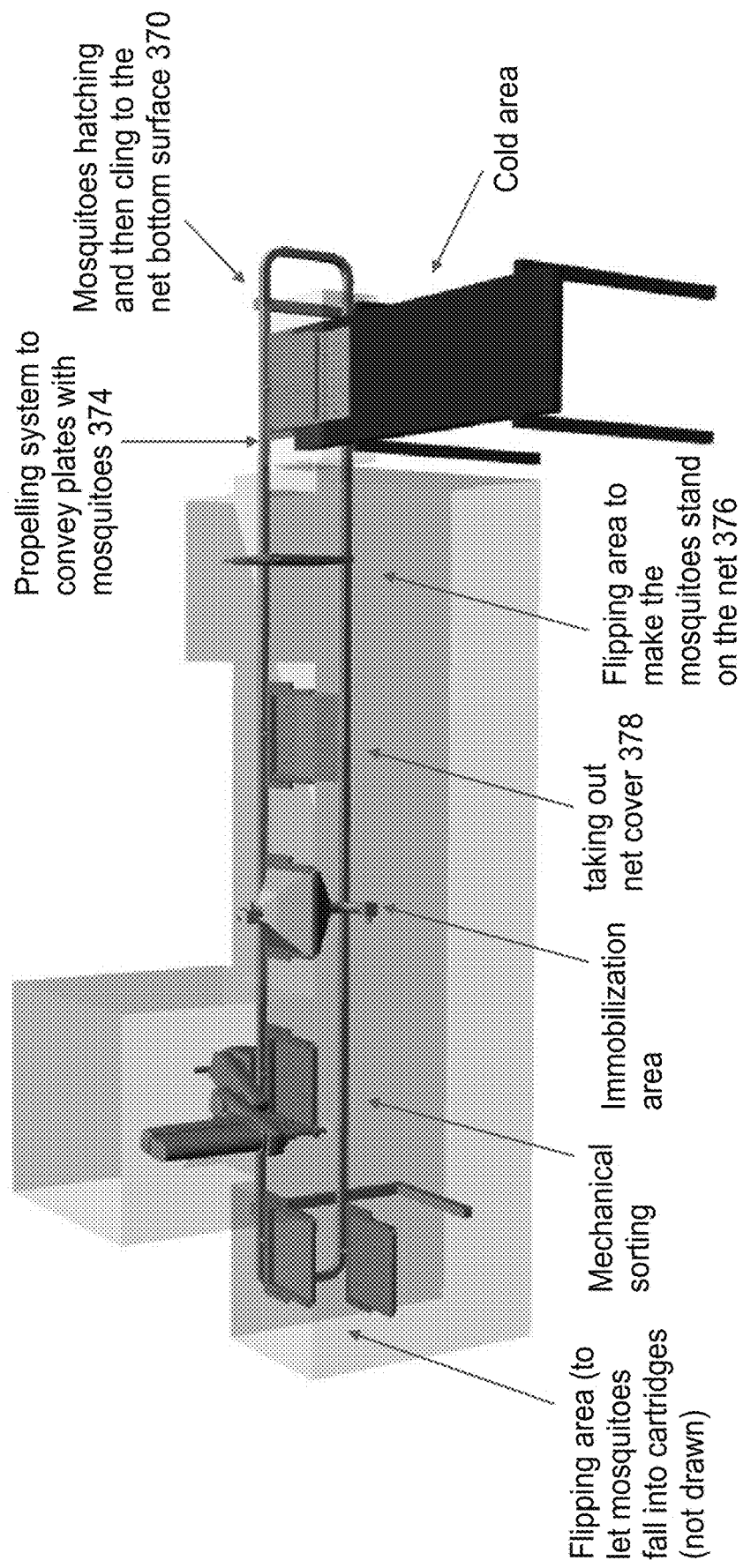

FIG. 35 shows a hatching area 370, where mosquitoes hatch and then move upwards and cling to netting. The netting is moved outwards 374 and flipped over 376 so that the mosquitoes are standing. The cover may be removed 378 if there is one, and immobilization, mechanical sorting and placing in cartridges is unchanged.

Figure 36:
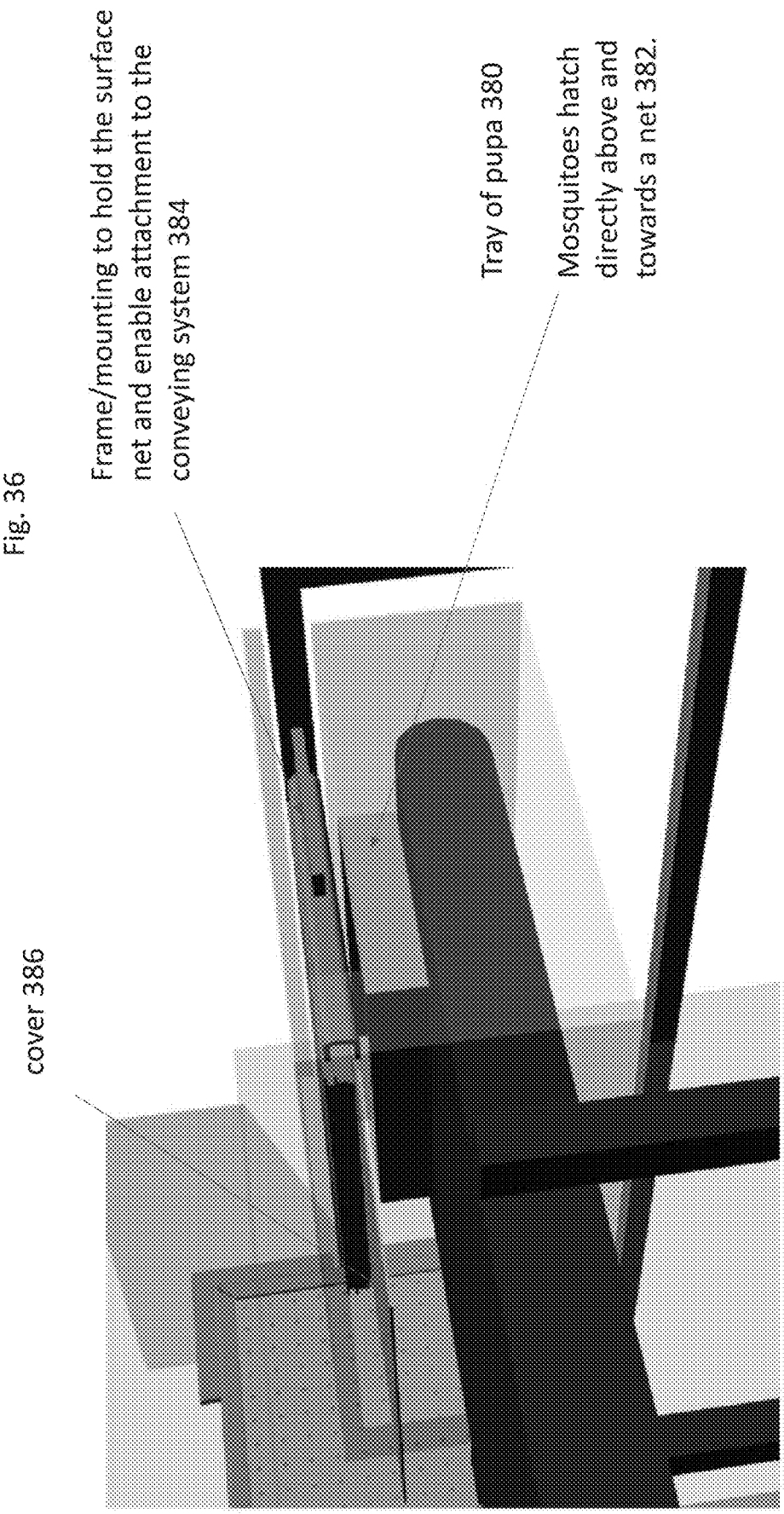

FIG. 36 is a detail of FIG. 35. A tray of pupae 380 is brought to the hatching area. Mosquitoes hatch and fly up towards the net 382. A frame or mounting 384 holds the net and allows for attachment to the conveyor system. Optionally a cover 386 is placed above to ensure that awake mosquitoes do not escape.

Figure 37:
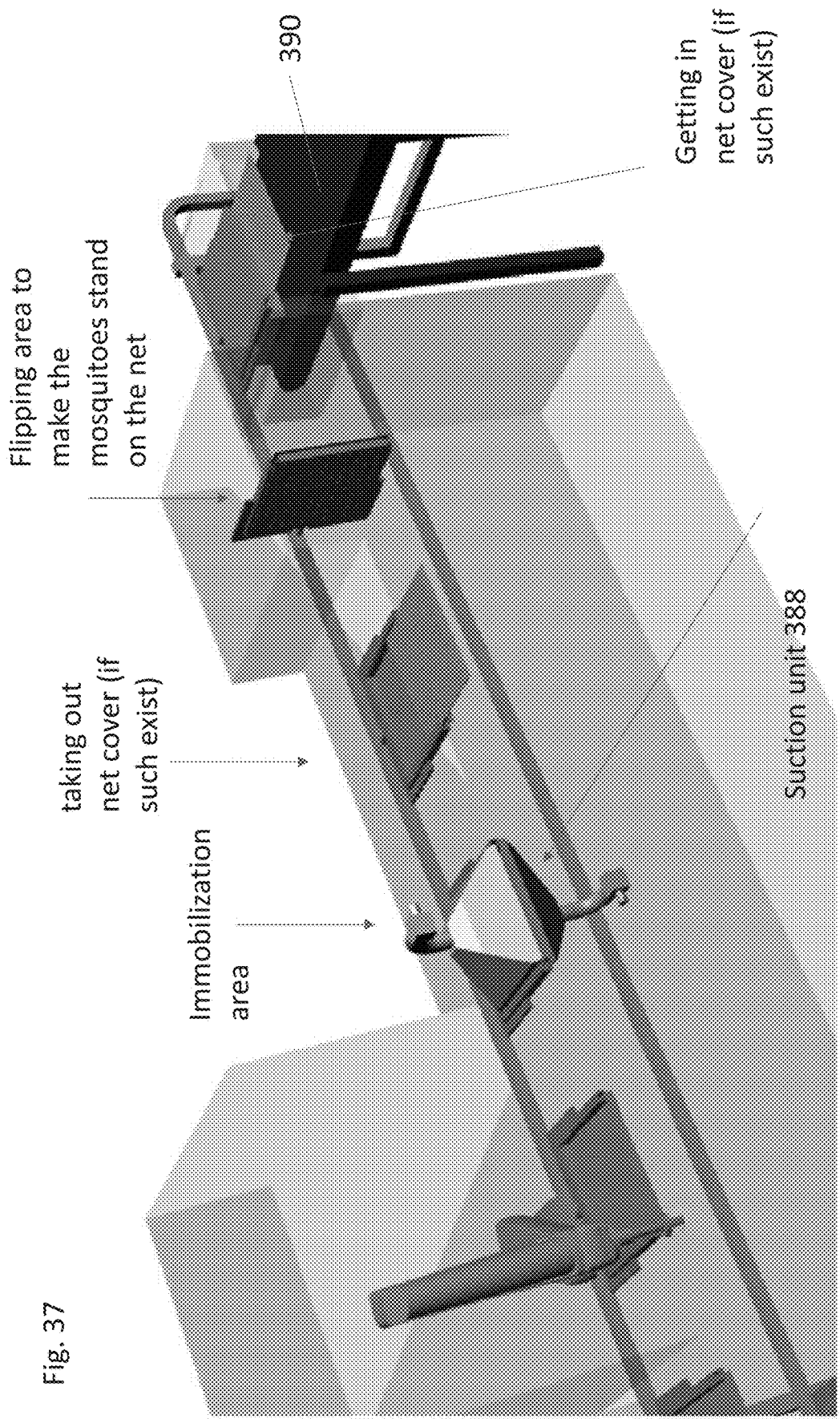

FIG. 37 is a further detail of FIG. 35. A suction unit 388 creates a pressure difference to support flow of cold air from above through the net. Conveyor 390 takes the plates onwards to the next section.

Figure 38:
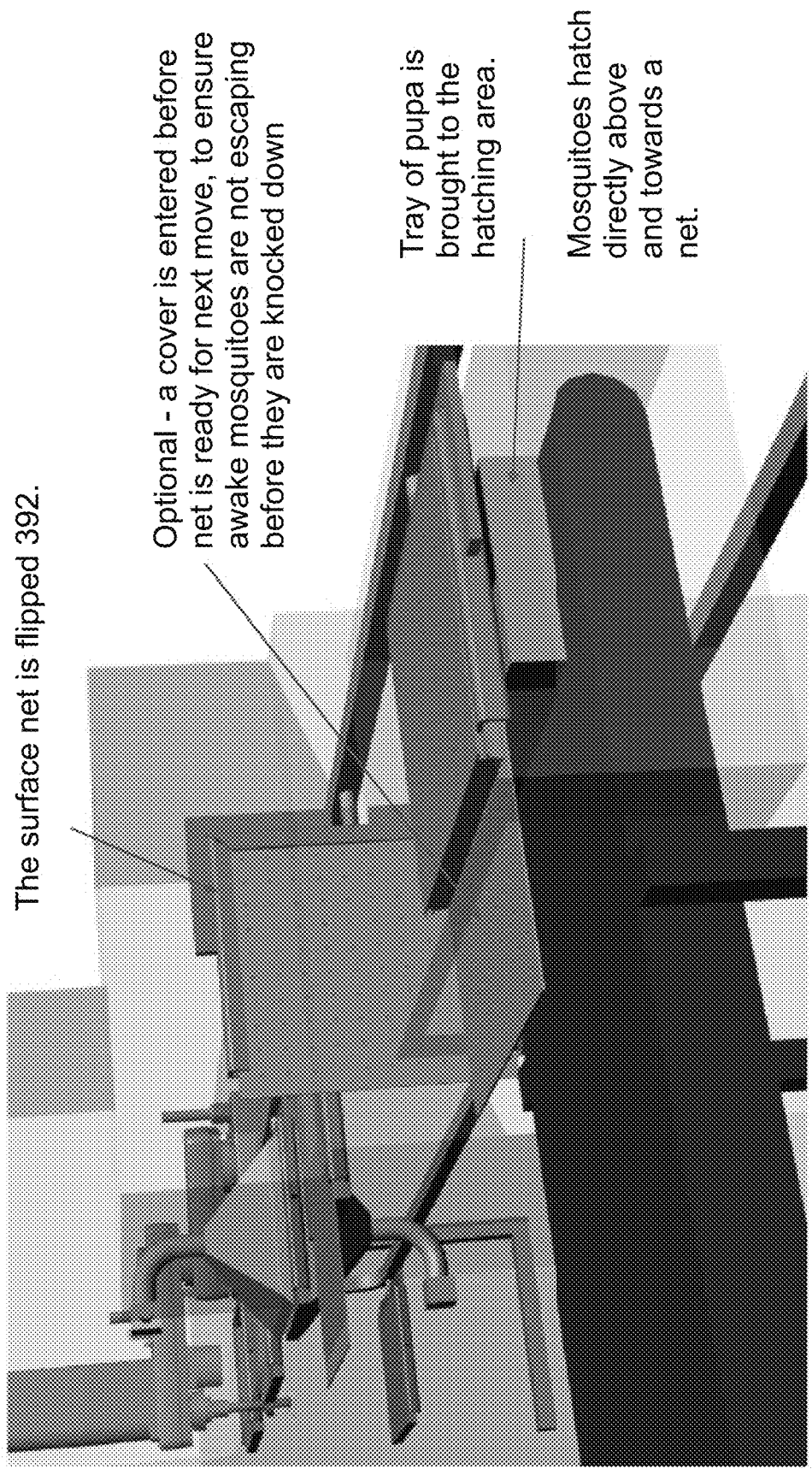

FIG. 38 is a further detail of FIG. 35 showing the net being flipped over to empty mosquitoes into a cartridge. The surface net is flipped 392 just before the insects are knocked down. Alternatively, the insects can first be knocked down and then the net flipped.

FIG. 39 is a diagram showing successive positions when the net is flipped over.

It is expected that during the life of a patent maturing from this application many relevant robot picking, vision and learning technologies will be developed and the scopes of the corresponding terms are intended to include all such new technologies a priori.

The terms "comprises", "comprising", "includes", "including", "having" and their conjugates mean "including but not limited to".

The term "consisting of" means "including and limited to".

As used herein, the singular form "a", "an" and "the" include plural references unless the context clearly dictates otherwise. For example, the term "a compound" or "at least one compound" may include a plurality of compounds, including mixtures thereof.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. Method of providing insects for classifying insects for sorting into classes or for quality control of sorted insects, the method comprising:

providing the insects in a container having a closable opening;

releasing the insects onto an air flow into a funnel, the air flow and the funnel carrying the insects to a collection location, the insects being collected on a conveyable surface of a movable conveyor, the conveyable surface being porous;

applying immobilizing agent to the insects on the collection location, thereby to provide stationary insects for said sorting or quality control;

applying a pressure gradient across said porous surface, said pressure gradient to ensure flow of air and preventing turbulence; and the insects being conveyed on said conveyable surface from said collection location.

2. The method of claim 1, wherein said immobilizing agent is one member of the group consisting of chilled air, carbon dioxide and ammonia, and an agent applied to said collection location.

3. The method of claim 1, wherein the immobilizing agent is released into said funnel to provide a confined area of immobility, and said collection location is on a moving conveyor, the confined area being openable to allow conveying of said insects therefrom.

4. The method of claim 3, further comprising providing multiple imaging locations around said conveyor to provide images of said immobilized insects for classification.

5. The method of claim 4, comprising obtaining at least one feature extraction from said imaging locations.

6. The method of claim 4, comprising obtaining classifications from each imaging location or from imaging locations and from extracted features, and applying a rule to decide between different classifications of a same insect.

7. The method of claim 3, providing a feeding station along said moving conveyor for feeding said insects.

8. The method of claim 1, wherein one of said classes is desired, the method comprising using a robot arm for removing insects of said desired class.

9. The method of claim 1, comprising drawing the insects to said collection location and inverting a surface at said collection location.

10. A method of classifying adult mosquitoes into male and female mosquitoes, comprising:
    obtaining a plurality of adult mosquitoes according to claim 1;
    immobilizing the mosquitoes;
    locating their forward body parts;
    imaging their forward body parts,
    from the imaging identifying the antenna, the maxillary palp, and the proboscis; and
    identifying at least one of the group consisting of:
    a male, the male being identified from at least one of a bushy antenna, a longer maxillary palp and a longer proboscis; and
    a female, the female being identified from at least one of a smooth antenna, a shorter maxillary palp and a shorter proboscis.

11. The method of claim 1, wherein said conveyor comprises a plurality of conveying sections.

12. The method of claim 1, comprising a robot arm for removing insects of a desired class for packing.

13. The method of claim 1, comprising providing a feeding station along said moving conveyor for feeding said insects.

14. Method of providing insects for sorting into classes comprising:
    providing a plurality of insects from a robot arm;
        placing each insect from said robot arm onto a collection location of a conveyable surface on a moving conveyor, the conveyable surface comprising a porous surface, said placing being at a predetermined location, thereby to form a pattern, from said plurality of insects, on said moving conveyor;
    continuing to place insects until said pattern is completely formed;
    applying immobilizing agent to the insects on the conveyable surface;
    applying a pressure gradient across said porous surface, said pressure gradient to ensure flow of air and preventing turbulence;
    conveying the insects, thereby to provide a flow of stationary insects for sorting.

15. The method of claim 14, wherein said collection location is on a collection plate large enough to take said plurality of insects, the method comprising continuing to place insects until a predetermined threshold is reached and then moving said conveyor.

16. The method of claim 15, wherein said pattern is placed on said conveyable surface.

17. The method of claim 16, wherein said immobilizing agent is one member of the group consisting of chilled air, carbon dioxide and ammonia and fluid applied to said conveyable surface.

18. The method of claim 16, wherein the immobilizing agent is released into a confined area of immobility on said moving conveyor, said confined area being opened to allow said conveying.

19. The method of claim 16, further comprising providing at least one imaging location around said conveyor to provide images of said immobilized insects for classification, or providing overlap between said imaging locations to enable following of a given insect between different imaging locations.

20. The method of claim 19, comprising obtaining feature extractions from said at least one imaging location.

21. The method of claim 19, comprising obtaining classifications from each of said at least one imaging location or from imaging locations and from extracted features, and applying a rule to decide between different classifications of a same insect.

22. The method of claim 21, wherein the classifications are male and female, the method comprising retaining any insect for which all classifications are male.

* * * * *